US005940178A

United States Patent [19]
Barber et al.

[11] Patent Number: 5,940,178
[45] Date of Patent: Aug. 17, 1999

[54] NEPHELOMETER AND TURBIDIMETER COMBINATION

[75] Inventors: Duane G. Barber; Songtai Tu, both of Yorba Linda; Richard P. Watts, Diamond Bar, all of Calif.

[73] Assignee: Beckman Instruments, Inc., Fullerton, Calif.

[21] Appl. No.: 08/674,780

[22] Filed: Jul. 3, 1996

[51] Int. Cl.[6] .......................... G01N 21/00; G01N 21/27; G01N 35/00; G01N 35/02
[52] U.S. Cl. .......................... 356/339; 356/300; 356/319; 356/322; 356/346; 422/63; 422/67; 422/82.05; 422/64; 422/82.09; 422/81; 422/102; 422/103; 436/43; 436/47; 436/50; 436/164; 436/165; 436/172
[58] Field of Search .................................. 422/63, 67, 64, 422/68.1, 82.05, 82.09, 81, 102, 103, 105; 356/300, 303, 322, 346, 339; 424/130.1; 436/536, 539, 805, 43, 47, 50, 164, 172, 165

[56] References Cited

U.S. PATENT DOCUMENTS

| | | |
|---|---|---|
| 3,967,901 | 7/1976 | Rodriquez . |
| 4,053,229 | 10/1977 | McCluney . |
| 4,110,044 | 8/1978 | Pettersson et al. . |
| 4,118,625 | 10/1978 | Underwood . |
| 4,140,395 | 2/1979 | Kreikebaum . |
| 4,140,902 | 2/1979 | Young . |
| 4,240,753 | 12/1980 | Brück . |
| 4,264,206 | 4/1981 | Hattori . |
| 4,325,910 | 4/1982 | Jordan . |
| 4,408,880 | 10/1983 | Tsuji et al. . |
| 4,420,256 | 12/1983 | Fladda et al. . |
| 4,547,070 | 10/1985 | Moll et al. . |
| 4,679,939 | 7/1987 | Curry et al. . |
| 4,697,925 | 10/1987 | Hyodo t al. . |
| 4,715,708 | 12/1987 | Ito . |
| 4,826,319 | 5/1989 | Namba et al. . |
| 4,896,961 | 1/1990 | Ito . |
| 4,920,275 | 4/1990 | Itoh . |
| 4,983,040 | 1/1991 | Chu et al. . |
| 4,990,795 | 2/1991 | Suzuki et al. . |
| 5,014,216 | 5/1991 | Stafford et al. . |
| 5,082,790 | 1/1992 | Theobald et al. . |
| 5,135,306 | 8/1992 | Kanebako et al. . |
| 5,198,369 | 3/1993 | Itoh et al. . |
| 5,294,806 | 3/1994 | Batchelder et al. . |
| 5,333,024 | 7/1994 | Maxey et al. . |

FOREIGN PATENT DOCUMENTS

| | | |
|---|---|---|
| WO8703960 | 7/1987 | European Pat. Off. . |
| WO9508774 | 3/1995 | European Pat. Off. . |

*Primary Examiner*—Ponnathapura Achutamurthy
*Assistant Examiner*—P. Ponnaluri
*Attorney, Agent, or Firm*—William H. May; P. R. Harder; Margaret A. Kivinski

[57] ABSTRACT

A nephelometer and nephelometer/turbidimeter combination of the type useful in automated chemical analyzers is provided. The combination includes a laser for generating a polarized laser beam having an S-wave component and a P-wave component. The beam is split by a beam splitter specially constructed so that a known proportion of one of the two polarized portions of the beam is directed to a reaction container. In the reaction container, a first polarized component of the laser beam is used in a nephelometric chemical analysis. The remainder of the laser beam passes through the beam splitter to a laser control light detector. Before the remainder of the laser beam reaches the laser control light detector, however, the polarized component which is not used in nephelometric chemical analysis is filtered out. The laser control detector uses the non-filtered portion of the laser beam to control the output of the laser. The combination also includes an LED which emits a beam of light at a longer wave length than that of the laser. Such beam of light is projected through the reaction container to a turbidimeter light detector. A second beam splitter is provided between the reaction container and the turbidimeter light detector to deflect the residual portion of the laser beam away from the laser. This prevents the residual portion of the laser beam from being reflected back into the reaction container.

30 Claims, 12 Drawing Sheets

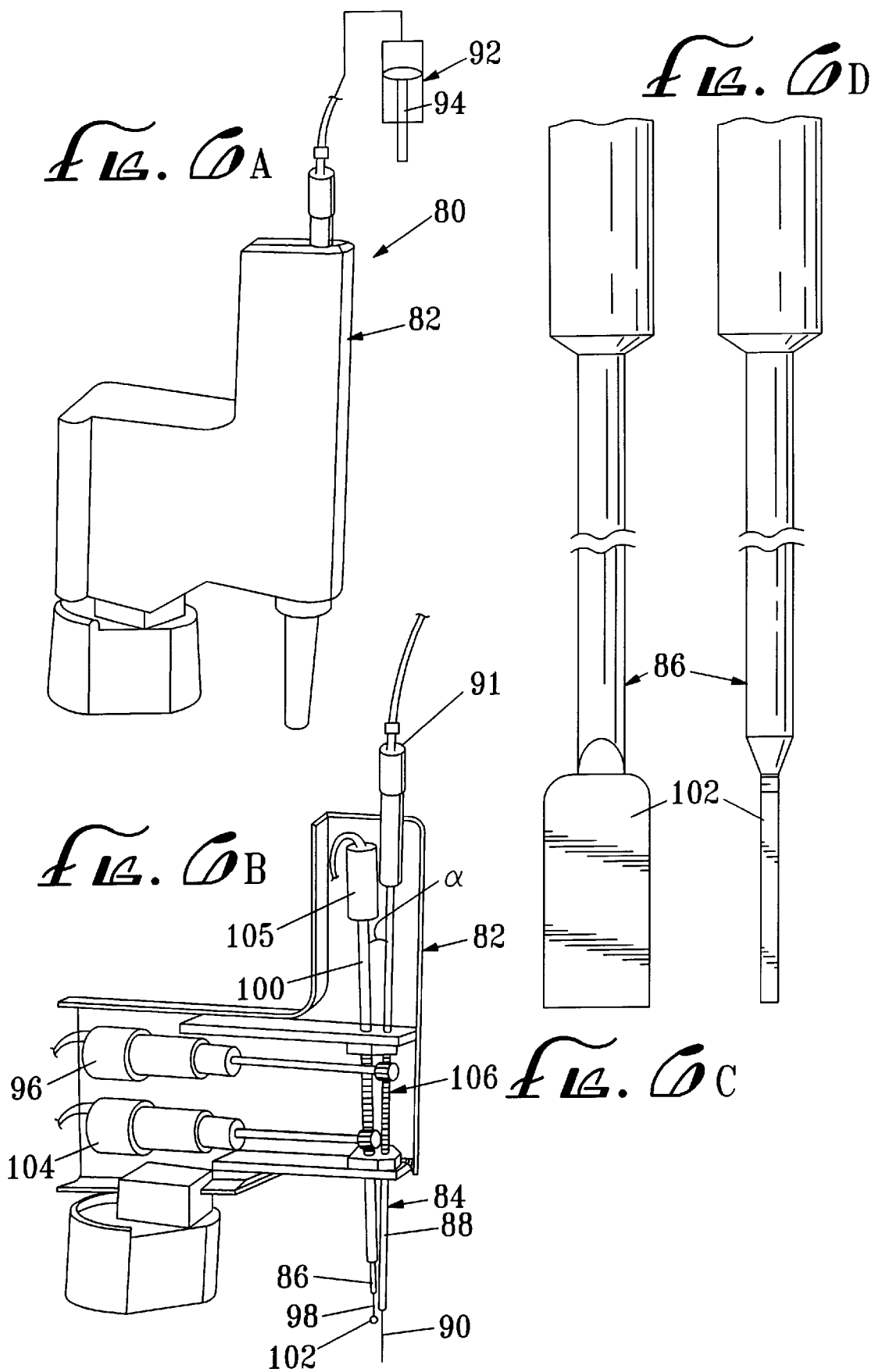

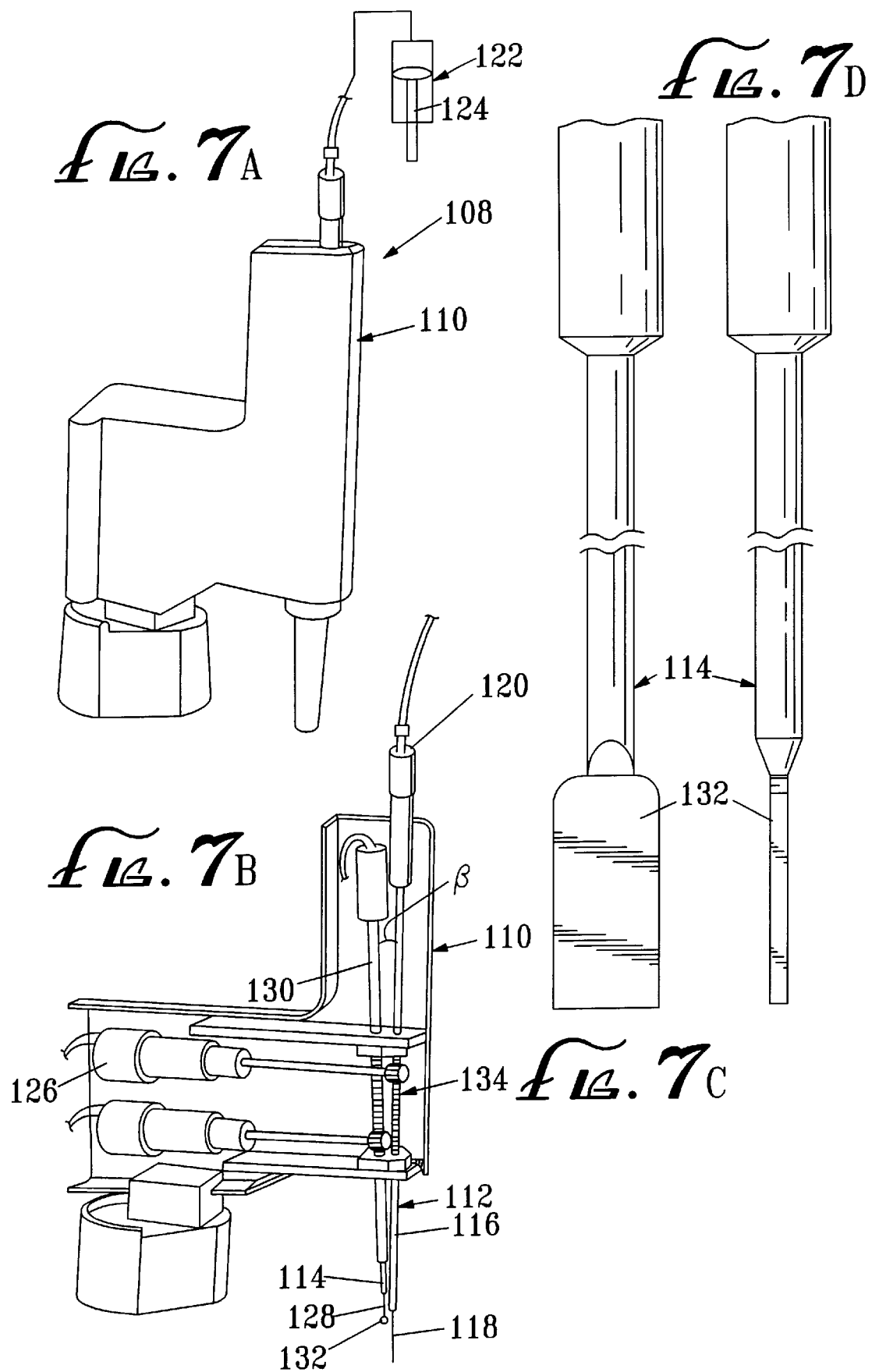

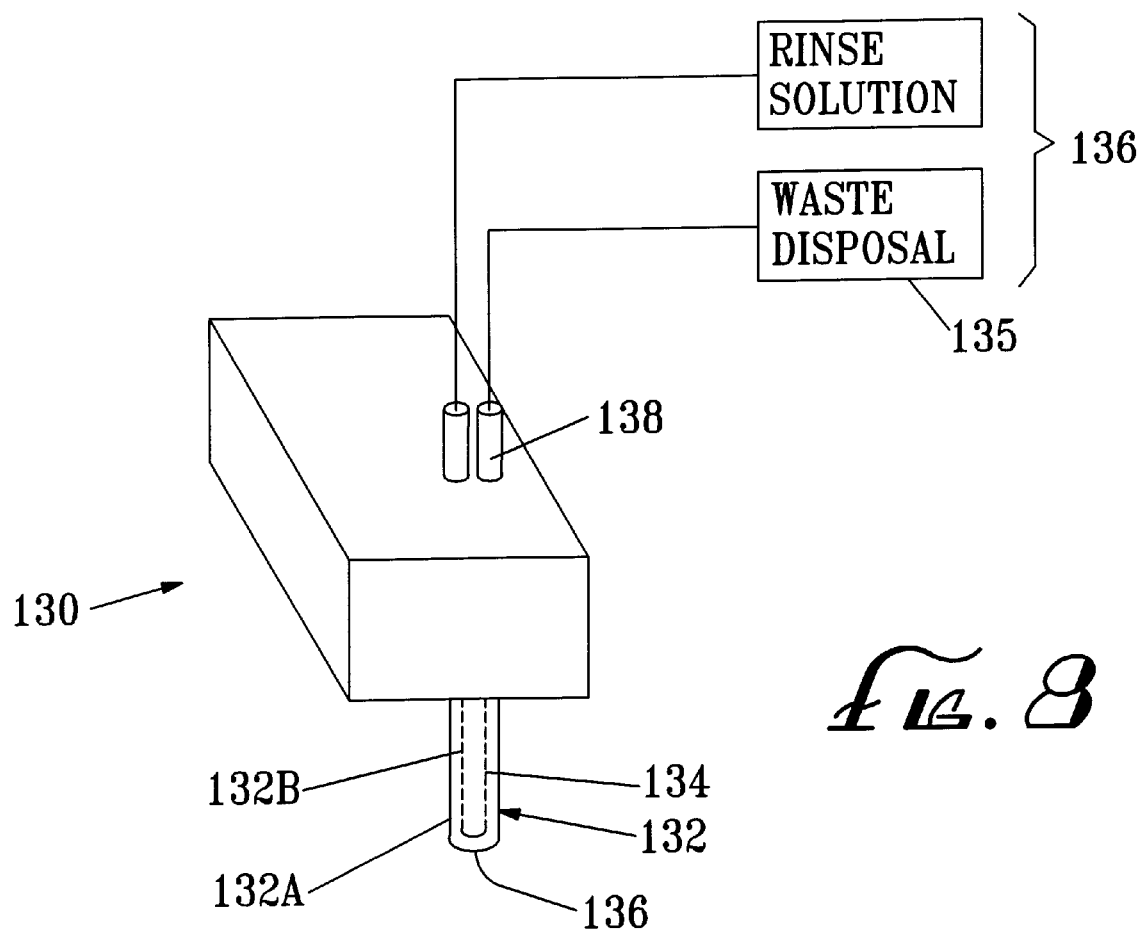

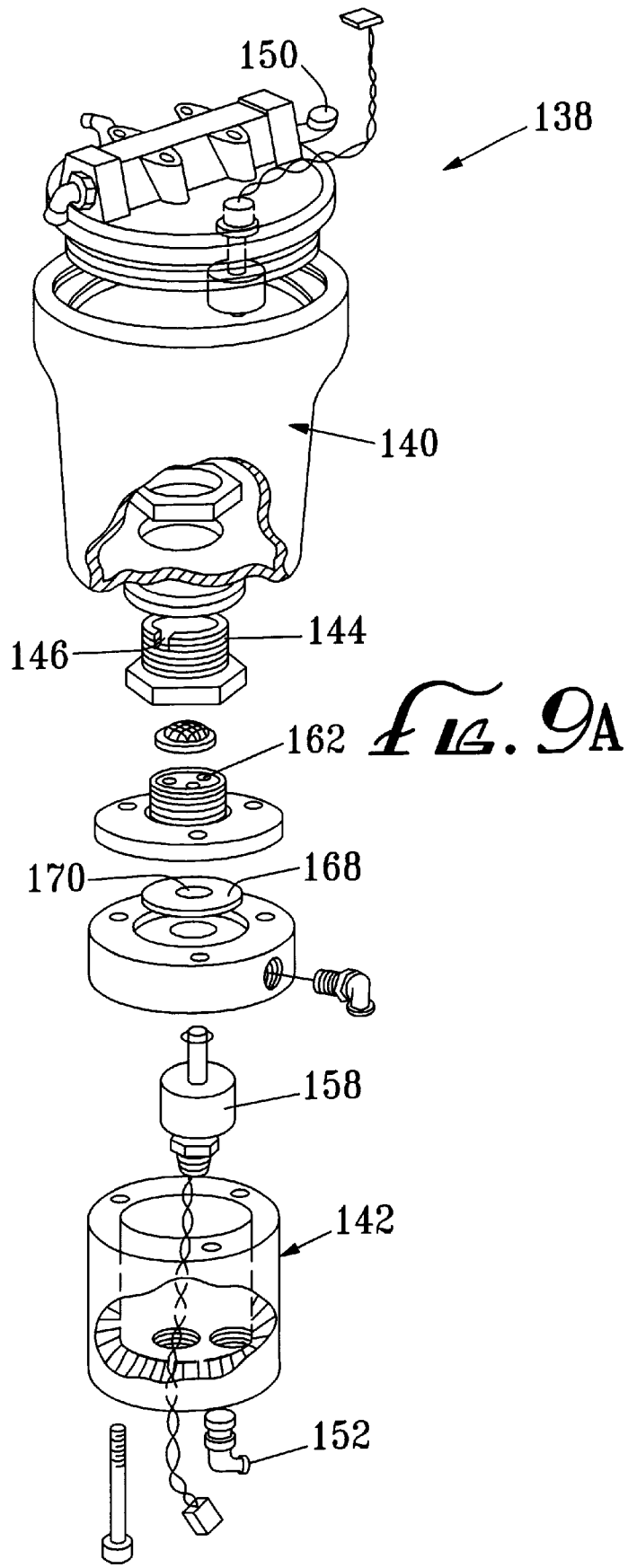

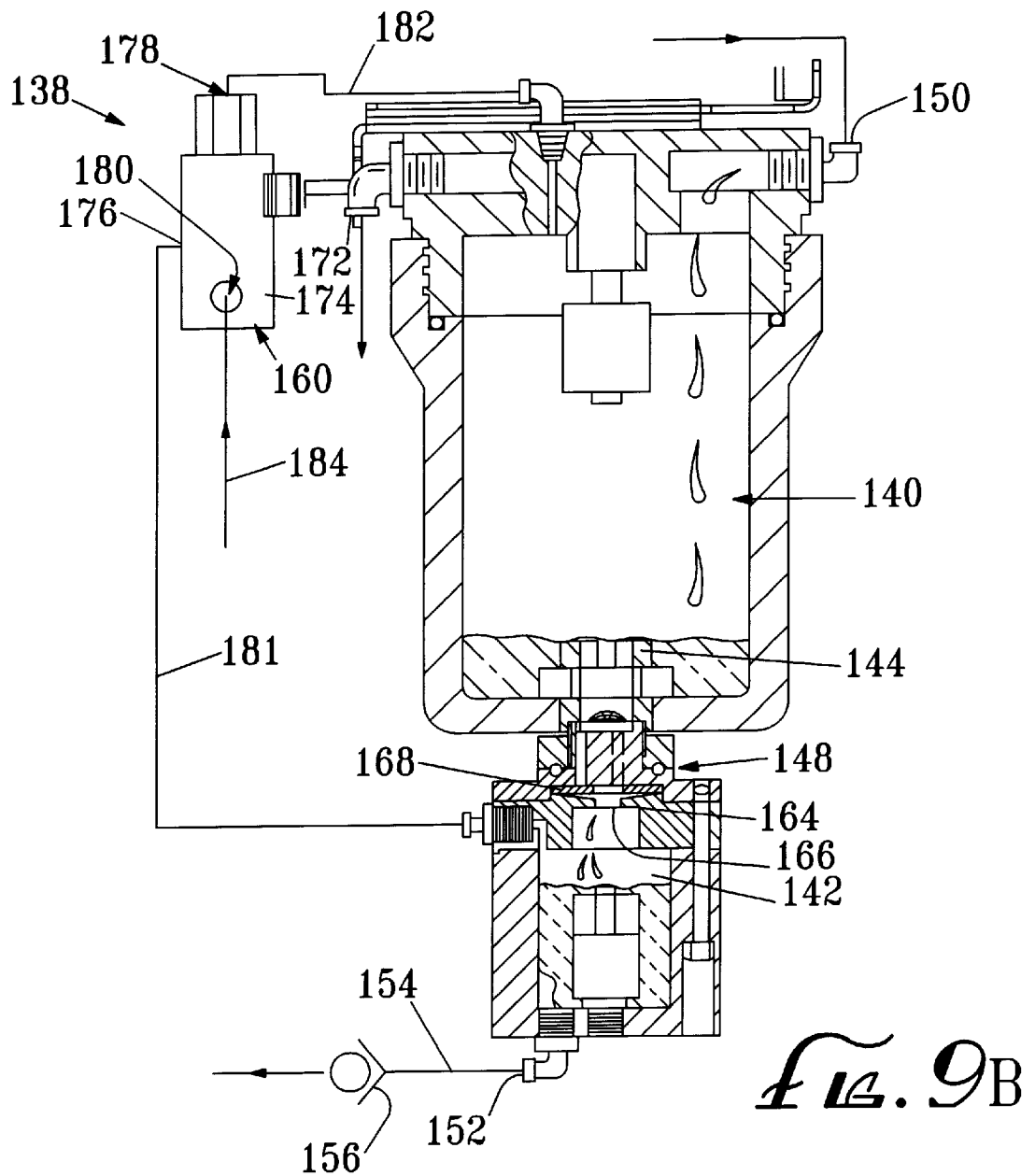
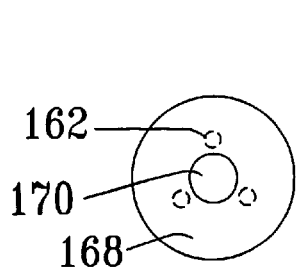
fig. 9B
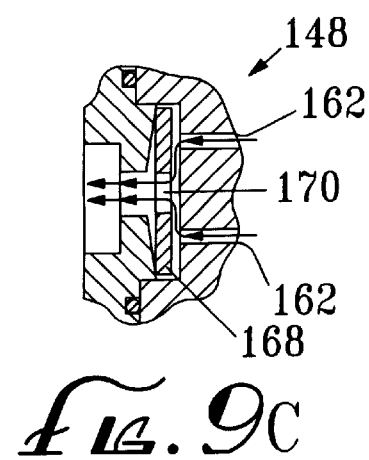
fig. 9D
fig. 9C

NEPHELOMETER AND TURBIDIMETER COMBINATION

FIELD OF THE INVENTION

This invention generally relates to the field of automated clinical chemical analyzers, and specifically to nephelometer/turbidimeter combinations useful in such automated clinical chemical analyzers.

BACKGROUND OF THE INVENTION

A number of different automated clinical chemical analyzers are known in the art. Such analyzers range from simple, largely manually-operated instruments to highly complex, nearly fully automated instruments. One class of clinical chemical analyzer which has proved very successful is a class of clinical chemical analyzers which employ a nephelometer and/or a turbidimeter as the operative analytic instrument. Such chemical analyzers have been found to be highly efficient in analyzing a wide variety of liquid chemical solutions, especially liquid chemical solutions of interest to medical hospital facilities and medical research laboratories.

In both nephelometry and turbidimetry, a light source is projected through a liquid sample retained within a transparent sample container. Particulate matter or other sources of turbidity within the liquid sample cause some of the incident light to scatter. The quantity of such scattered light can be closely correlated to at least one parameter of the sample. Generally, nephelometry uses a light source having a relatively short wave length (e.g., 500 nm–800 nm) and is effective in detecting very small particulate matter. Turbidimetry, on the other hand, generally uses light sources having longer wave lengths (e.g., 800 nm–1100 nm) and is effective in detecting particulate matter of larger size. The theory of nephelometry and turbidimetry as used in automated chemical analyzers is discussed in detail in U.S. Pat. No. 5,296,195, which is incorporated herein by reference.

As sophisticated and efficient as modern automated chemical analyzers using nephelometry and turbidimetry combinations have become today, several problems continue to exist. A first problem is control of the laser commonly used in such machines. Typically, such laser produces a light beam which is highly polarized, having a P-wave component and an S-wave component. In most cases, scattering from only one of these polarized components is measured in the analysis machine. Unfortunately, prior art machines have attempted to regulate the power output from the laser by controlling the total energy from the laser beam, including both polarized components. Attempting to control the laser in this way has proved unsatisfactory because a variation in the relative percentage of the two polarized components within the total beam is not perceived by the controlling mechanism. Thus, the light energy of the polarized portion actually used in the analysis machine may vary from test to test. This adversely affects the reliability and accuracy of the analytical process.

A second problem with such automated analyzing machines of the prior art arises because some of the polarized light from the laser is commonly reflected off of the turbidimeter light receptor focusing lens back into the analysis container. Some of this polarized light is scattered by the sample in the analysis container and is measured by the nephelometer light receptor. This may result in the nephelometer receptor registering a falsely high reading. This phenomenon also adversely affects accuracy and reliability of the analytical process.

Accordingly, there is a need for a nephelometer analyzing system and a nephelometer/turbidimeter combination which is more accurate and more reliable than systems of the prior art.

SUMMARY OF THE INVENTION

The invention satisfies these needs. The invention is a nephelometer comprising (a) a laser for generating a polarized laser beam of variable energy intensity, the laser beam having a first polarized moiety and a second polarized moiety; (b) a laser control light detector for detecting light energy and generating a control signal corresponding to the quantity of such detected light energy; (c) a first beam splitter positioned to direct a first portion of the first polarized moiety of the laser beam into a transparent reaction container and to direct a second portion of the first polarized moiety of the laser beam to the first light detector, the first beam splitter being constructed so that the light energy of the second portion of the first polarized moiety is a known fraction of the total light energy output of the first polarized moiety; (d) a nephelometer light detector positioned to detect light energy scattered from the first polarized moiety of the first portion of the laser beam by particles suspended in a liquid medium within the reaction container; (e) a polarizing filter oriented to filter out the second polarized moiety of the second portion of the laser beam without substantially affecting the first polarized moiety of the second portion of the laser beam, the polarizing filter being positioned between the first beam splitter and the laser control light detector; and (f) a control circuit for controlling the total output of the first polarized moiety of the laser beam using the control signal generated by the laser control light detector.

The invention is also a nephelometer and turbidimeter combination comprising (a) a laser for generating a laser beam having a first wave length; (b) a first beam splitter positioned to direct the laser beam into a transparent reaction container along a specific light path; (c) a nephelometer light detector positioned to detect light energy scattered from the laser beam by particles suspended in a liquid medium within the reaction container; (d) a light emitting diode for generating a light beam having a second wave length and directing that light beam through the reaction container along the specific light path; (e) a turbidimeter light detector positioned along the specific light path on the opposite side of the reaction container from the light emitting diode; (f) a focusing lens positioned between the reaction container and the turbidimeter light detector for focusing the light beam to the turbidimeter light detector; and (g) a second beam splitter positioned between reaction cuvette and the lens for reflecting the laser beam away from the focusing lens.

Typically, the reaction container is a reaction cuvette.

Typically, the laser is a visible diode laser emitting light at a wave length between about 600 and about 850 nm, most typically between about 650 and about 700 nm.

In a preferred embodiment, the proportion of the first polarized moiety in the first portion of the laser beam is between about 50% and 99% of the polarized moiety of the total identity in the output of the laser beam, more preferably between about 90% and about 97%, and most preferably between about 95% and about 97%.

The first polarized moiety can be an S-wave moiety and the second polarized moiety can be a P-wave moiety. In other embodiments, the first polarized moiety can be a P-wave moiety and the second polarized moiety can be an S-wave moiety.

Typically, the light emitting diode is capable of emitting light at a wave length between about 850 and 1050 nm.

The invention is also a combination of the rate nephelometer and the nephelometer/turbidimeter combination described above.

The invention is also an automated chemical analyzer which incorporates the nephelometer and/or nephelometer/turbidimeter combination described above.

The invention provides a uniquely accurate and reliable nephelometer and nephelometer/turbidimeter combination, without unduly increasing manufacturing costs or operating expenses.

DESCRIPTION OF THE DRAWINGS

These and other features, aspects and advantages of the present invention will become better understood with reference to the following description, appended claims and accompanying drawings where:

FIG. 6A is a perspective view of a sample probe arm assembly having features of the invention;

FIG. 6B is a cut-away view of the sample probe arm assembly shown in FIG. 6A;

FIG. 6C is a front view of a sample stirring rod useful in the invention;

FIG. 6D is a side view of the sample stirring rod shown in FIG. 6C;

FIG. 7A is a perspective view of a reagent probe arm assembly having features of the invention;

FIG. 7B is a cut-away view of the reagent probe arm assembly shown in FIG. 7A;

FIG. 7C is a front view of a reagent stirring rod useful in the invention;

FIG. 7D is a side view of the reagent stirring rod shown in FIG. 7C;

FIG. 8 is a perspective view of a cuvette wash station useful in the invention;

FIG. 9A is an exploded view of a waste trap assembly having features of the invention;

FIG. 9B is a cross-sectional view of the fully assembled waste trap assembly shown in FIG. 9A;

FIG. 9C is a cross-sectional side detail view of a valve useful in the waste trap assembly shown in FIGS. 9A and 9B;

FIG. 9D is a plan view of a flexible disk useful in the waste trap assembly shown in FIGS. 9A–9C;

DETAILED DESCRIPTION OF THE INVENTION

The following discussion describes in detail one embodiment of the invention and several variations of that embodiment. This discussion should not be construed, however, as limiting the invention to those particular embodiments. Practitioners skilled in the art will recognize numerous other embodiments as well. For a definition of the complete scope of the invention, the reader is directed to the appended claims.

Figure 11:
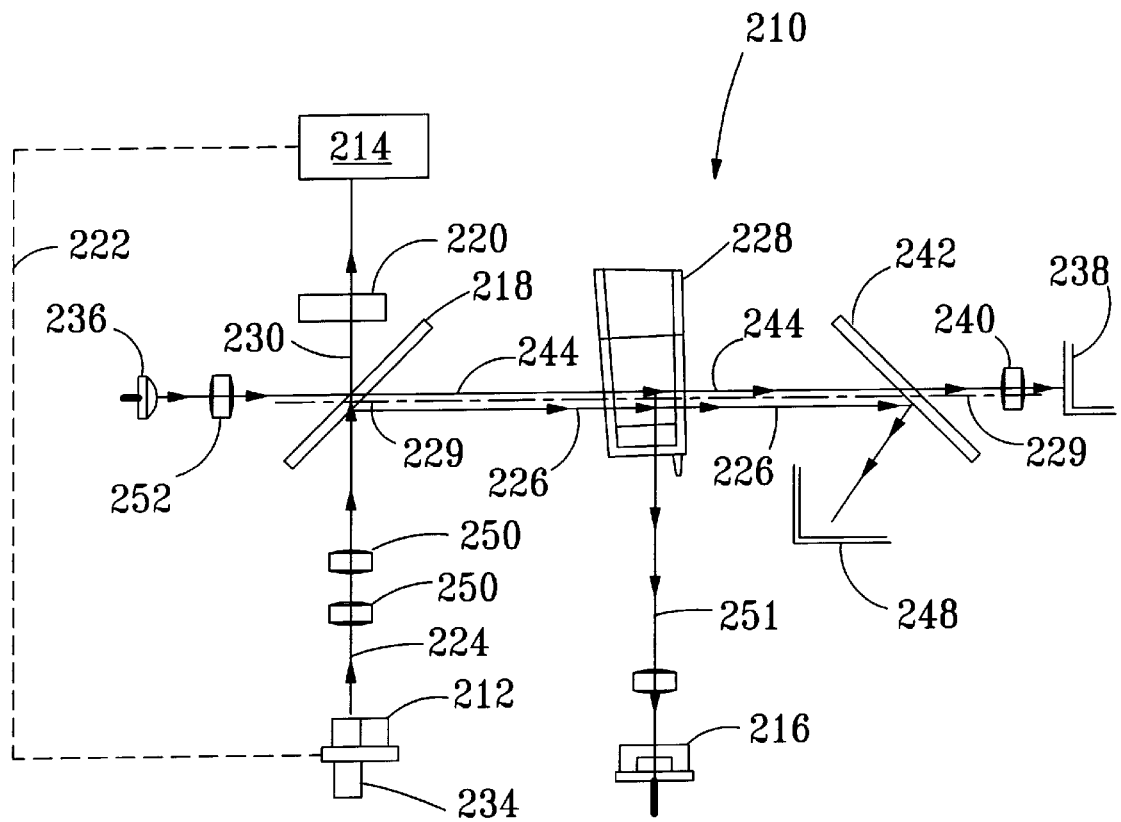
FIG. 11 is a schematic view of a nephelometer/turbidimeter combination having features of the invention.

The invention 210 is a nephelometer/turbidimeter combination as shown in FIG. 11. The nephelometer comprises a laser 212, a laser control light detector 214, a nephelometer light detector 216, a first beam splitter 218, a polarizing filter 220 and a control circuit 222.

The laser 212 is typically a visible diode laser emitting light at a wave length between about 600 and about 850 nm. In one preferred embodiment, the laser 212 emits light at a wave length between about 650 and about 700 nm, most preferably at about 670 nm.

Typically, the laser 212 is capable of emitting between about 1 and about 10 milliwatts of total light energy. A commercially available laser usable in the invention is manufactured by Toshiba of Japan as Toshiba Model No. TOLD9225 670 Laser Diode.

The light beam 224 produced by the laser 212 typically has a first polarized moiety and a second polarized moiety. The first polarized moiety may be an S-wave component and the second polarized moiety may be a P-wave component. In other embodiments, the first polarized moiety is the P-wave component and the second polarized moiety is the S-wave component.

The laser control light detector 214 detects a portion of the light energy emitted from the laser and generates a control signal corresponding to the quantity of such light energy detected. The laser control detector 214 can be a high sensitivity silicon photodiode detector such as that which is manufactured by Hamamatsu of Japan as Hamamatsu Model No. S1223-01PIN silicon high sensitivity photodiode.

The first beam splitter 218 is positioned to direct a first portion 226 of the laser beam into a transparent reaction container 228 along a specific path 229 and to direct a second portion 230 of the laser beam 224 to the laser control light detector 214. It is important that the first beam splitter 218 be constructed so that the light energy of the second portion 230 of the laser beam 224 is a known fraction of the total laser beam 224.

Typically, the proportion of the first portion 226 is between about 50% and about 99% of the total light energy of the output of the laser beam 224. Preferably, however, the proportion of the first portion 226 of the laser beam 224 is between about 90% and 99% of the total light energy in the output of the laser beam 224, most preferably between about 95% and about 97%.

The nephelometry light detector 216 is positioned to detect light energy scattered from the first polarized moiety of the first portion 226 of the laser beam 224 by particles suspended in a liquid medium within the reaction container 228. Where the first polarized moiety is the S-wave component of the laser beam 224, the nephelometer light detector 216 is positioned at 90° to the first portion 226 of the laser beam 224 as the first portion 226 enters the reaction container 228.

Like the laser control detector 214, the nephelometer light detector 216 can be a high sensitive silicon photodiode detector such as that which is manufactured by Hamamatsu of Japan as Hamamatsu Model No. S1223-01PIN silicon high sensitivity photodiode.

The first beam splitter 218 is typically a dichroic beam splitter constructed to split light having the wave length emitted by the laser 212. The first beam splitter 218 is constructed so that the light energy of the second portion of the laser beam 224 is a predetermined and constant fraction of the total light energy output of the laser beam 224.

The polarizing filter 220 is positioned between the first beam splitter 218 and the laser control light detector 214. The polarizing filter 220 is oriented to filter out the second polarized moiety of the second portion 230 of the laser beam 224 without substantially affecting the first moiety of the second portion 230 of the laser beam 224. The polarizing filter 220 can be any appropriate polarizer, such as is manufactured by the Polaroid Corporation as Polaroid Model No. HN 22 ×0.035 " thickness.

The control circuit 222 is designed using prior art techniques to control the total output of the first polarized moiety of the laser beam 224 using the control signal generated by the laser control light detector. The control circuit 222 includes control circuitry which carries the control signal from the laser control light detector 214 to a laser beam controller 234. The laser beam controller 234 is capable of increasing or decreasing the total energy output of the laser beam 224 to the control signal. In this way, the laser controller 234 controls the first polarized moiety in the first portion 226 of the laser beam 224 at a constant level.

Thus, it can be seen that, because the first portion 226 of the laser beam 224 is a known fraction of the total light energy output of the laser beam 224, the total light energy of the first polarized moiety in the second portion 230 of the laser beam 224 (that portion of the laser beam 224 being used to analyze the sample within the sample container 228) is maintained at a constant value.

The invention is also a rate nephelometer and rate turbidimeter combination comprising the laser 212, the nephelometry light detector 216, the first beam splitter 218, a light emitting diode 236, a turbidimeter light detector 238, a focusing lens 240 and a second beam splitter 242.

The light emitting diode 236 is designed and constructed to generate a light beam 244 having a wave length which is different than the wave length of the laser beam 224. The light emitting diode 236 is positioned to direct its light beam 244 through the reaction container 228 along the specific light path 229. In a typical embodiment, the light emitting diode 236 emits a light beam 244 having a wave length between about 850 and about 1040 nm. In one preferred embodiment, the wave length of such light beam 244 is about 940 nm. The light emitting diode 236 can be any of the commonly known light emitting diodes available in the art. A light emitting diode which can conveniently be used in the invention is an infrared emitting diode sold by Hamamatsu of Japan as Hamamatsu Model No. L2388(940NM).

The turbidimeter light detector 238, like the laser control and nephelometer light detectors 14 and 16, can be a high sensitivity silicon photodiode detector such as that sold by Hamamatsu of Japan as Hamamatsu Model No. S1223-01PIN silicon high sensitivity photodiode.

The focusing lens 240 is positioned between the reaction container 228 and the turbidimeter light detector 238 for focusing the light beam 244 emitted by the light emitting diode 236 to the turbidimeter light detector 238.

The second beam splitter 242 is positioned between the reaction container 228 and the focusing lens 240. The second beam splitter 242 is designed and positioned to reflect the first portion 226 of the laser beam 224 away from the focusing lens 240, preferably to a light sink 248.

In operation, the laser 212 is engaged to emit a laser beam 224 which travels through a pair of laser beam focusing lenses 250 to the first beam splitter 218. The first beam splitter 218 splits the laser beam 224 into a first portion 226 and a second portion 230.

The first portion 226 of the laser beam 224 is reflected along the specific light path 229 into a transparent reaction container 228 which contains a sample being analyzed. In the reaction container 228, the first polarized moiety of the first portion 226 of the laser beam 224 scatters in the direction of the nephelometer light detector 216. The degree of such scattering 251 is sensed by the nephelometer light detector 216 and is reported to a suitable controller (not shown) for correlation with a particular parameter of the analysis sample.

The remainder of the laser beam 224 which is not scattered continues along the specific light path 229 out of the reaction container 228 towards the focusing lens 240. Before such remainder of the laser beam 224 reaches the focusing lens 240, however, it is reflected by the second beam splitter 242 in a direction away from the focusing lens 240, preferably to a suitable light sink 248.

The second portion 230 of the laser beam 224 passes through the first beam splitter 218 and continues in a direction towards the laser control light detector 214. Before it reaches the laser control light detector 214, however, it passes through the polarizing filter 220 which filters out all of the second polarized moiety of this second portion 230 of the laser beam 224 (without substantially affecting the first moiety). Accordingly, the only light reaching the laser control light detector 216 is the first polarized moiety of the second portion 230 of the laser beam 224. This light is detected by the laser control light detector 216 and a signal corresponded to the energy of the light is transmitted via the control circuitry 222 to the laser controller 234.

Contemporaneously, light emitted from the light emitting diode 236 passes through a first lens 252, then through the first beam splitter 218 along the specific light path 229. Some of the light 244 from the light emitting diode 236 is scattered by the sample within a reaction container 228. All of the light 244 from the light emitting diode 236, however, continues generally along the specific light 229 path towards the focusing lens 240 and to the turbidimeter light detector 238. At the turbidimeter light detector 238, the degree of light non-scattering of the light from the light emitting diode 236 is measured and a signal is transmitted to a suitable analysis device (not shown) which correlates the measurement with a second parameter of the analysis sample.

Because the second beam splitter 242 reflects the residual laser beam 226 away from the focusing lens 240, little of this residual laser beam 226 is reflected off of the focusing lens 240 back through the beam splitter 242 and again into the reaction container 228. Accordingly, the amount of light scattering measured by the nephelometer light detector 216 is an accurate reflection of the first parameter of the analysis sample being investigated.

Figure 1:
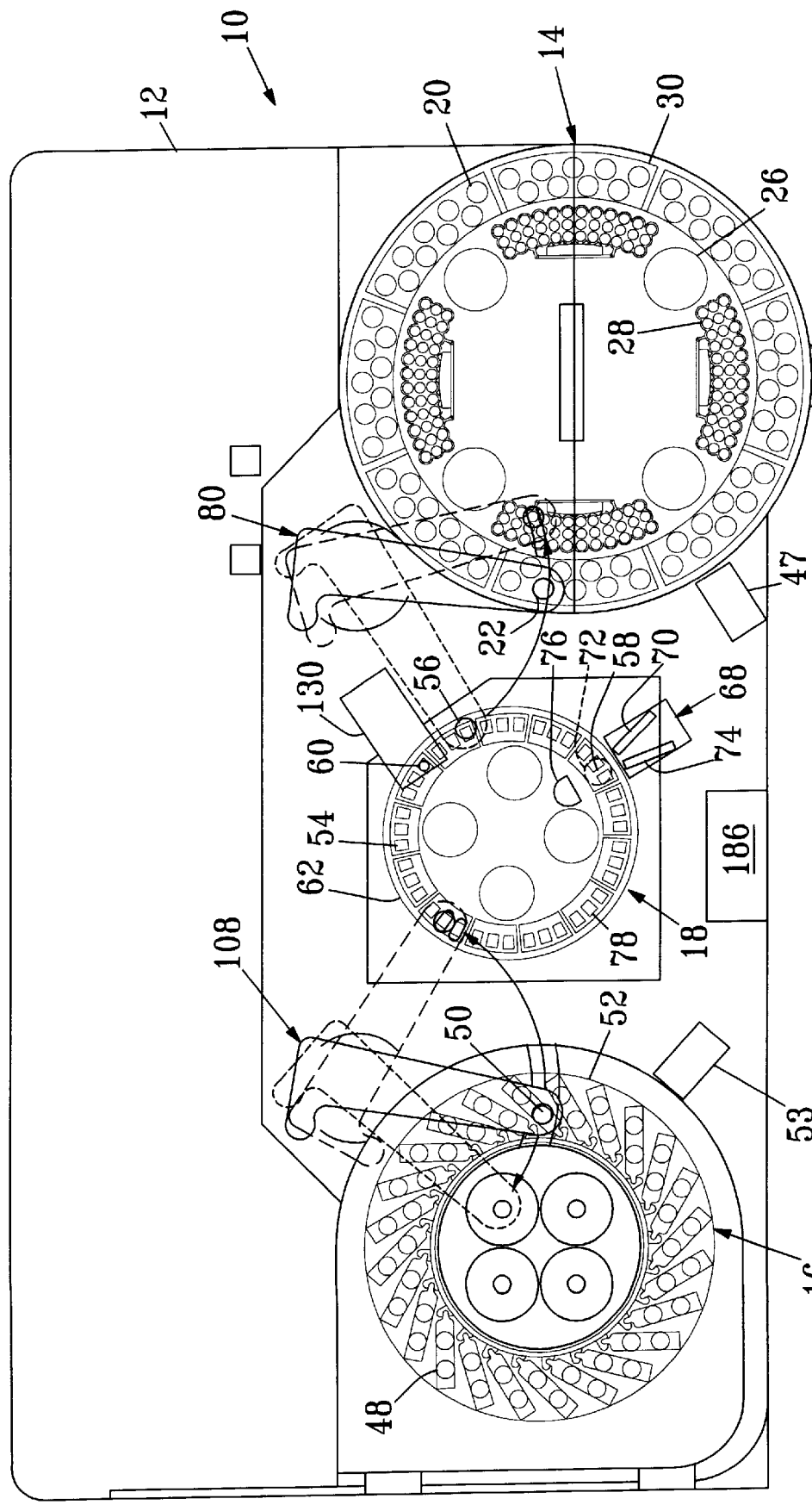
FIG. 1 is a schematic plan view of an automated analyzing machine having features of the invention.
Figure 2:
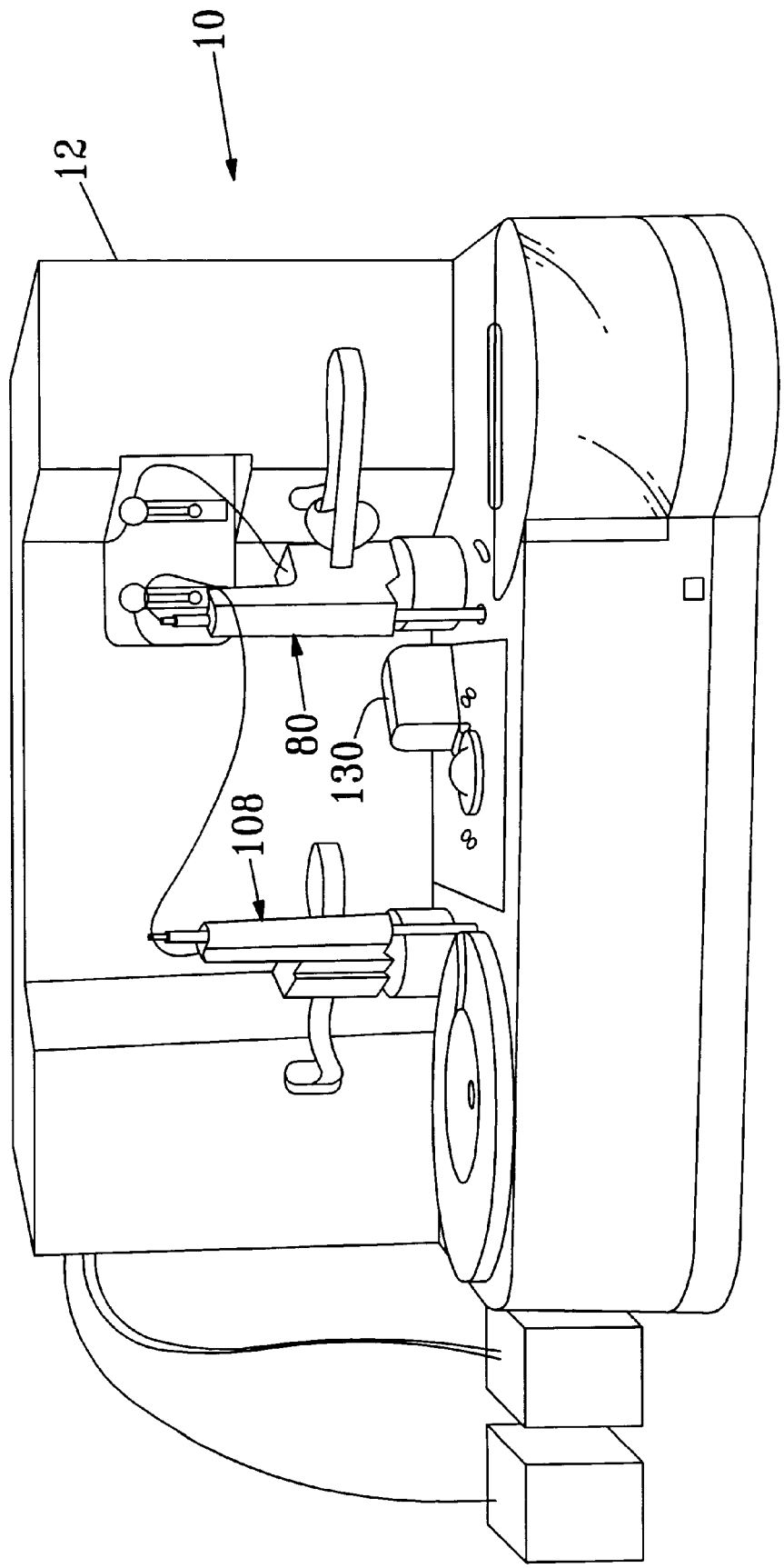
FIG. 2 is a front view of an automated analyzing machine having features of the invention.

The nephelometer and nephelometer/turbidimeter combination 210 of the invention can be incorporated into an automated analysis machine having significantly increased accuracy and reliability over similar machines of the prior art. Such a machine 10 is shown in FIGS. 1 and 2. The machine 10 comprises a body 12, a sample station 14, a reagent station 16 and a random access analyzing station 18.

The body 12 is generally a cabinet providing a housing for the various operative components used in the analyzing machine 10. The body 12 is typically made from a lightweight metal such as a lightweight sheet steel. The body 12 can include a canopy (not shown) for fully enclosing the operative components of the machine 10.

The sample station 14 is sized and dimensioned to retain a plurality of sample containers 20. The sample station 14 has at least one sample extraction site 22.

Figure 3:
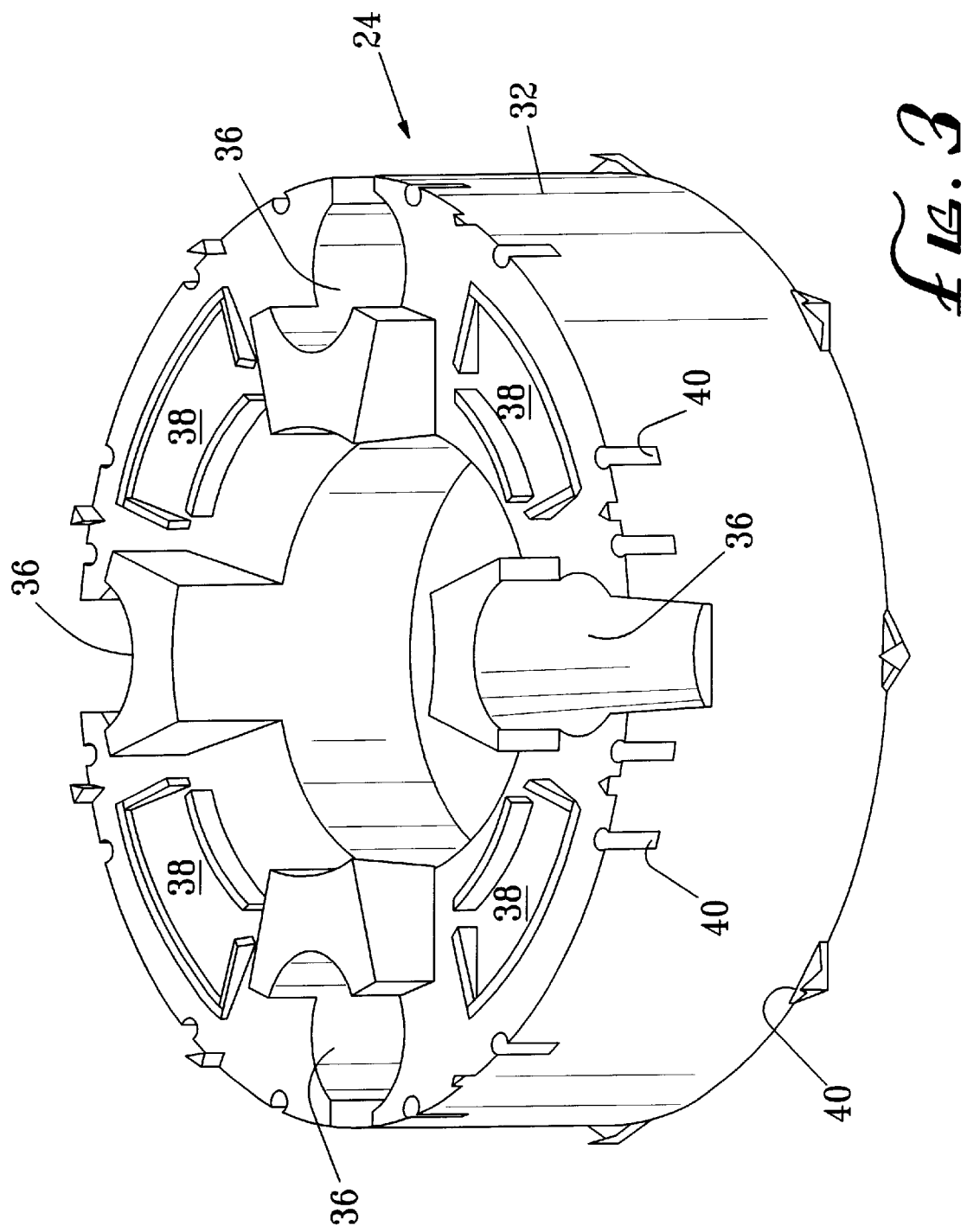
FIG. 3 is a perspective view of a sample carousel having features of the invention.

The sample station 14 preferably comprises a revolving sample carousel 24 as illustrated in FIG. 3. Typically, the sample carousel 24 is made from a lightweight metal or molded plastic. The sample carousel 24 is preferably sized and dimensioned to retain a plurality of sample containers 20, one or more diluent containers 26, and a plurality of dilution sections 28.

In the embodiment shown in the drawings, the sample carousel 24 comprises a carousel retainer assembly 40 for retaining a sample plurality of container racks 30 on the exterior wall 32 of the sample carousel 24. Such retainer assembly 40 can be resilient clips as shown in the embodiment illustrated in the drawings.

Figure 10:
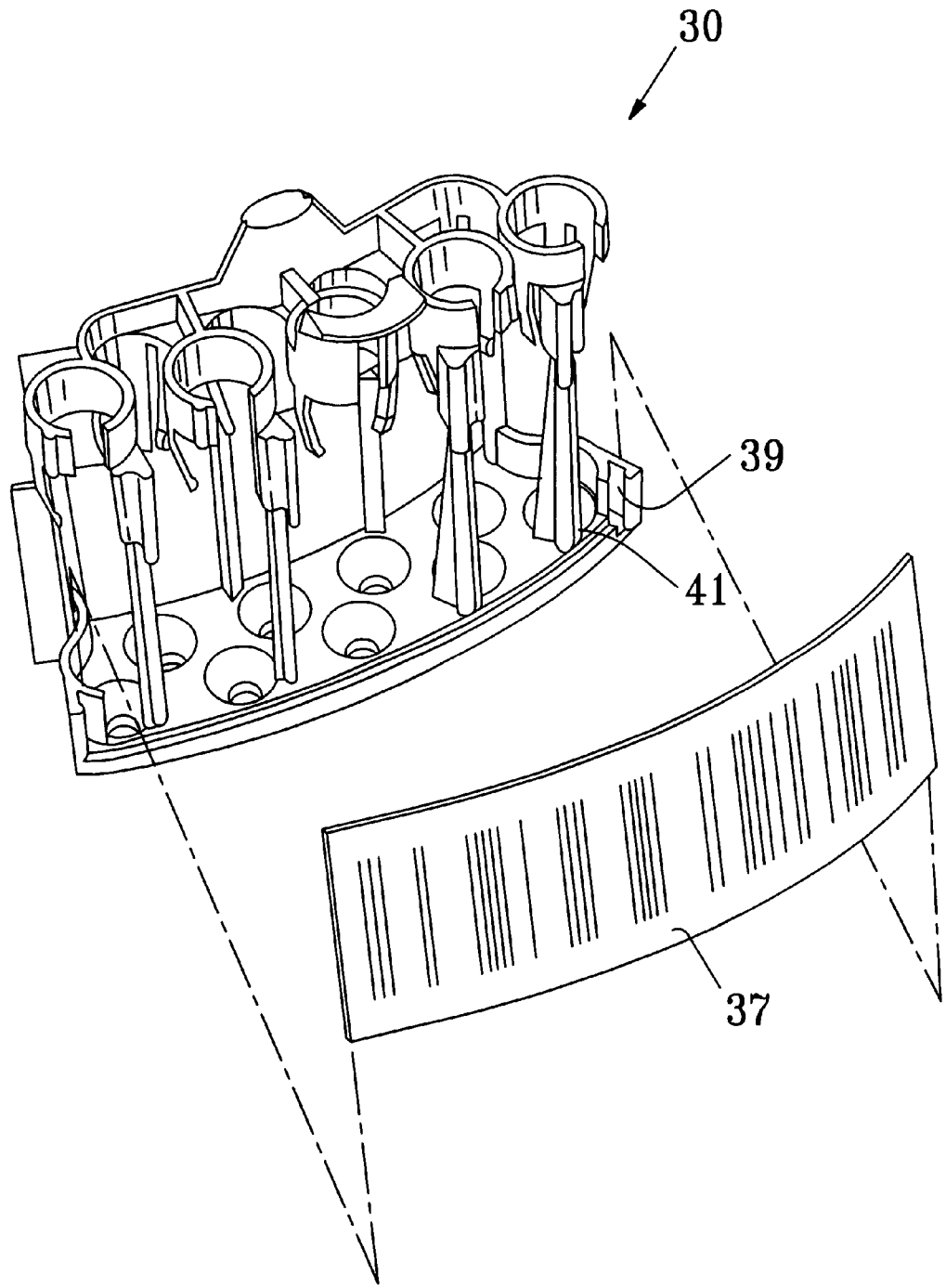
FIG. 10 is a perspective view of a sample container rack having features of the invention.

The sample rack 30 preferably comprises a sample container rack retainer assembly 39 for retaining a card 37 displaying bar-coded information on the forward wall 41 of the sample container rack 30. Such sample container rack retainer assembly 39 can be slots as shown in the embodiment illustrated in FIG. 10. However, many other ways of attaching the bar-coded card 37 to the forward wall 41 of the sample container rack 30 can also be used as well, including clamps, clips, prongs, snaps, buttons, hook and loop fasteners, pins, etc. It is preferable that the sample container rack retainer assembly 39 allows the operator to quickly and easily attach and later de-attach a bar code card 37 from the forward wall 41 of the sample container rack 30, most preferably without the use of tools.

In this embodiment, each sample container rack 30 houses nine individual sample containers 20 in a generally upright disposition.

Figure 4A:
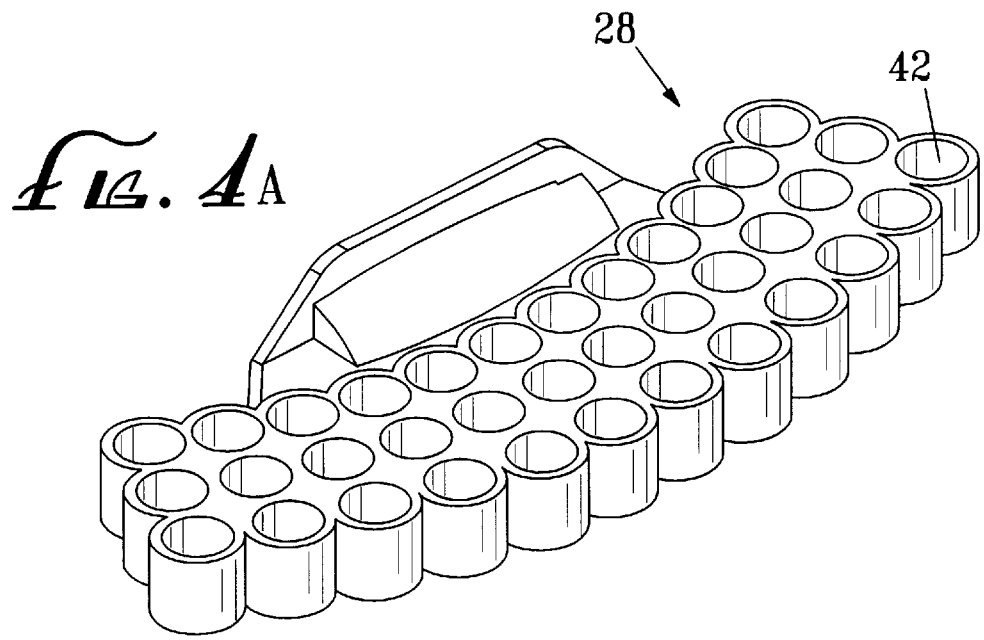
FIG. 4A is a perspective view of a dilution section having features of the invention.
Figure 4C:
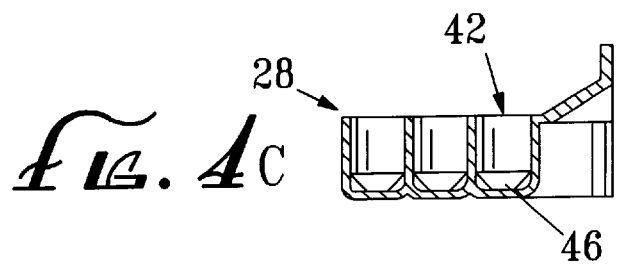
FIG. 4C is a cross-sectional side view of the dilution section shown in FIG. 4B, taken along line 4C—4C.
Figure 4B:
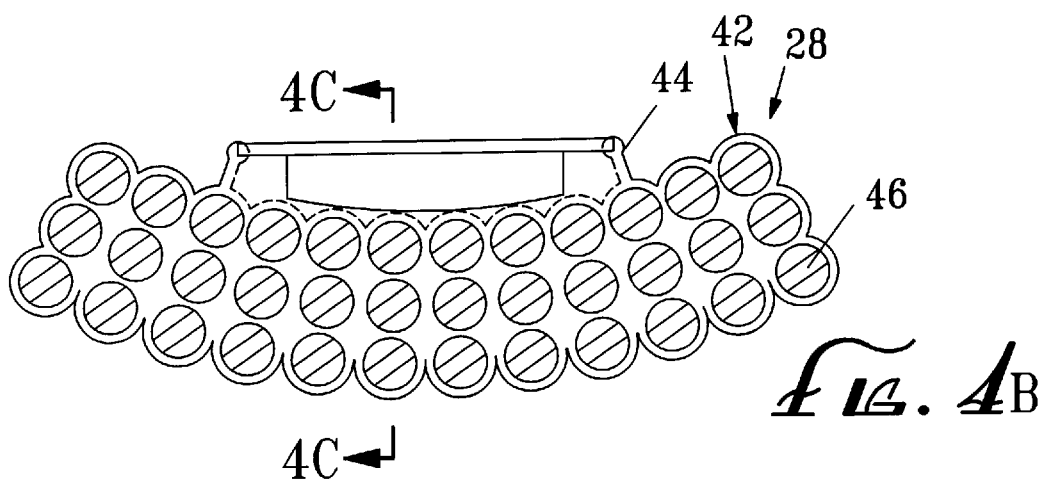
FIG. 4B is a plan view of the dilution section of FIG. 4A.
Figure 4D:
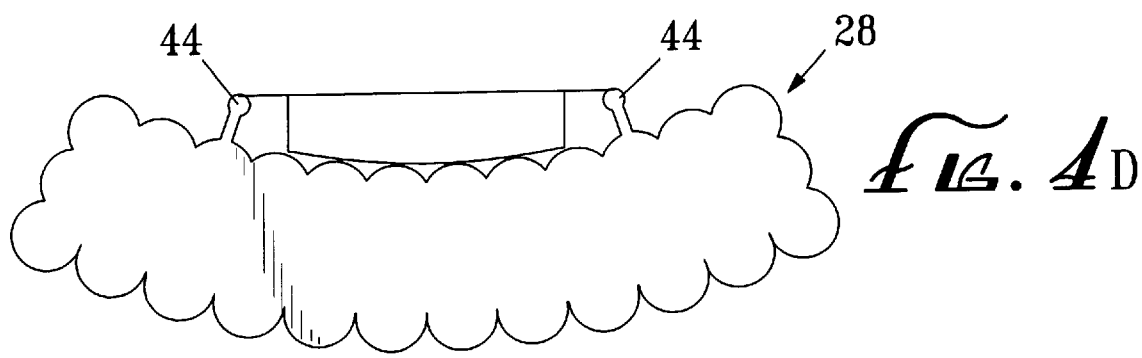
FIG. 4D is a bottom side view of the dilution container shown in FIGS. 4A–4C.

The sample carousel 24 shown in FIG. 3 has four diluent container retention locations 36 and four dilution section retention locations 38. The dilution sections 28 each comprise a plurality of dilution cups 42 as shown in FIGS. 4A–4C. Typically, each dilution section 28 is made from a molded plastic. Preferably, each dilution section 28 is easily installed and removed from the sample carousel 24 for ease of cleaning. It is also preferable that the dilution sections 28 be easily and quickly installed into and deinstalled from the sample carousel 24 without use of tools. The embodiment shown in the drawings has resilient nodes 44 which allow the dilution sections 28 to snap fit in the dilution section retention locations 38.

Each dilution cup 42 holds between about 0.01 and about 1.0 milliliters of liquid. As shown in FIG. 4C, each dilution cup 42 is tapered at the bottom to form a dilution cup narrow well 46 so that small amounts of liquid within the dilution cup 42 puddle within the narrow well and thereby remain easily extractable from the dilution cup 42. Each dilution cup narrow well 46 typically can retain between about 10 microliters and about 100 microliters. This feature minimizes reagent waste. This feature is especially important where the dilution cups 42 are made from a plastic material which is hydrophobic. In such cases, small amounts of liquid within the dilution cups 42 tend to bead instead of puddling, making it difficult to extract the liquid from the dilution cup 42.

The sample carousel 24 is movable by a rotating motor (not shown) such that each sample container 20 disposed on the sample carousel 24 can be alternatively positioned under and moved away from the one sample extraction site 22.

Preferably, the sample station 14 further comprises a sample station bar code reader 47 for reading bar-coded information on the sample containers 20 within the sample station 14 and/or on a bar code card 37 disposed on the forward wall 41 of the sample container rack 30.

The reagent station 16 is sized and dimensioned to retain a plurality of reagent containers 48 and has at least one reagent extraction site 50. A particularly useful reagent container 48 usable in the machine of the invention is described in detail in U.S. patent application Ser. No. 08/675,586, now abandoned, entitled "Reagent Cartridge", which is filed contemporaneously herewith and which is also incorporated herein by reference in its entirety. The reagent station 16 is movable within the body such that individual reagent containers 48 disposed within the reagent station 16 can be alternatively moved to and away from the reagent extraction site 50.

Like the sample station 14, the reagent station 16 preferably comprises a rotatable reagent carousel 52, typically made from a lightweight metal or molded plastic. The reagent carousel 52 is rotated by a reagent station motor (not shown).

Preferably, the reagent station 16 is refrigerated, such as to a temperature of about 15° C. Such refrigeration preserves reagent life and minimizes reagent evaporation.

Preferably, the reagent station 16 further comprises a reagent station bar code reader 53 for reading bar-coded information on reagent containers 20 within the reagent station 16 and/or on the exterior of the reagent carousel 24.

The random access analyzing station 18 is sized and dimensioned to retain a plurality of reaction cuvettes 54 of the type commonly known in the nephelometric and turbimetric arts. The random access analyzing station 18 comprises at least one cuvette mixing site 56, one random access analyzing station analyzing site 58 and a cuvette washing site 60.

Like the sample station 14 and the reagent station 16, the random access analyzing station 18 preferably comprises a rotatable carousel 62 which is rotated by a random access analyzing station motor (not shown).

Figure 5A:
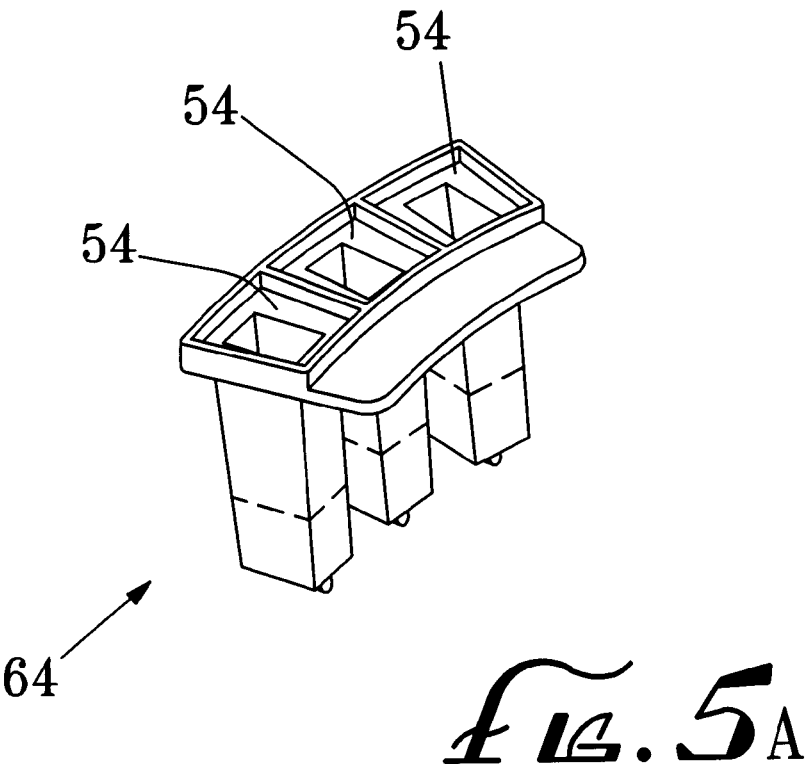
FIG. 5A is a perspective view of a reaction cuvette module useful in the invention.
Figure 5B:
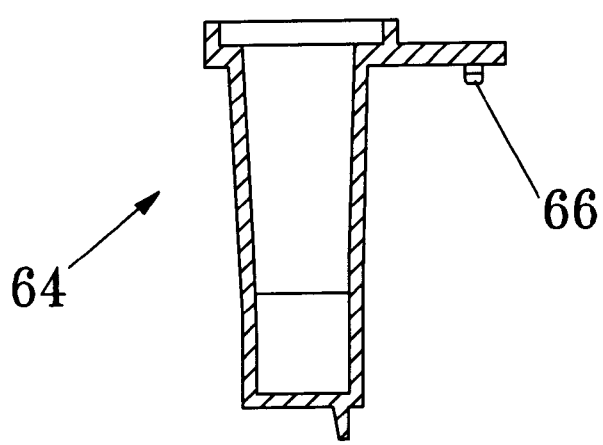
FIG. 5B is a cross-sectional side view of the reaction cuvette module shown in FIG. 5A.

In the embodiment shown in the drawings, the reaction cuvettes 54 are disposed in cuvette modules 64, each cuvette module 64 containing three individual cuvettes 54. The cuvette modules 64 are shown in FIGS. 5A and 5B. Each cuvette module 64 has prongs 66 to facilitate firm attachment to the random access analyzing station carousel 62. To minimize the cost of expensive reagent, it is important that the cuvettes 54 be made as small as practically possible.

In most applications, it is preferable that the random access analyzing station 18 be operatable at a fixed elevated temperature, such as about 37° C. To accomplish this, the random access analyzing station 18 preferably includes means for circulating heated air upwardly through the random access analyzing station 18.

The random access analyzing station 18 further comprises a random access analyzing station analyzer 68 which is disposed proximate to the random access analyzing station analyzing site 58 for determining at least one parameter of a sample disposed within a cuvette 54 within the random access analyzing station 18. In a preferred embodiment, the random access analyzing station analyzer 68 is the nephelometer and turbidimeter combination 310 of the invention.

Preferably, the random access analyzing station 18 further comprises an onboard control sample 78. Such onboard control sample 78 allows the user to program the machine to automatically calibrate the random access analyzing station analyzer 68 during normal operation of the machine 10. This feature maximizes accuracy and reliability over similar machines of the prior art. This feature also increases throughput by eliminating the need to periodically shut down the machine 10 to calibrate the random access analyzing station analyzer 68. A particularly useful onboard control sample usable in the invention is described in detail in U.S. patent application Ser. No. 08/675,587, now U.S. Pat. No. 5,741,441, entitled "Non-Liquid Scatter Standard", which is filed contemporaneously herewith and which is incorporated herein by reference in its entirety.

The analysis machine 10 of the invention further comprises a sample probe arm assembly 80 such as shown in FIGS. 6A–6D. The sample probe arm assembly 80 includes a sample probe arm 82, a hollow sample probe 84 and a rotatable sample stirring rod 86. The sample probe 84 has an internal chamber 88, an open lower end 90 and an open upper end 91. A sample probe pressure altering assembly 92 is provided to alternatively place pressure or a vacuum on the internal chamber 88. Preferably, the pressure altering assembly 92 comprises a syringe 94.

The sample probe 84 is disposed generally vertically in the sample probe arm 82 and is movable by a sample probe motor 96 between a lower sample probe position and an upper sample probe position.

The sample stirring rod 86 has a lower end 98, an upper end 100 and a stirring rod paddle 102. The sample stirring rod 86 is also disposed generally vertically in the sample probe arm 82 and is movable by a sample stirring rod motor 104 between a lower sample stirring rod position and an upper sample stirring rod position. The sample stirring rod is operatively rotated by a sample stirring rod rotating motor 105.

Preferably, the raising and lowering of the sample stirring rod 86 is independent of the raising and lowering of the sample probe 84. This provides speed and flexibility over important similar devices in the prior art which can only raise and lower the stirring rod 86 at the same time that the probe 84 is raised and lowered.

Preferably, the sample stirring rod 86 and the sample probe arm 84 are both raised and lowered using a rack and pinion assembly 106. Such rack and pinion assembly 106 allows the sample probe 84 and the reagent probe 86 to be mounted close enough to one another to achieve the close proximities of their respective lower ends 90 and 98 described immediately below.

The sample probe 84 and the sample stirring rod 86 are disposed within the sample probe arm 82 at a slight angle with respect to one another. Preferably, this angle $\alpha$ is between about 2.4° and about 2.6°. The sample probe 84 and the sample stirring rod 86 are angled towards one another so that, when both the sample probe 84 and the sample stirring rod 86 are at their respective lower positions, the distance between the lower end 90 of the sample probe 84 and the lower end 98 of the sample stirring rod 86 is between about 1.7 mm and about 5.3 mm, more preferably between about 1.7 mm and about 3.5 mm, most preferably between about 1.7 mm and about 3 mm. By structuring the sample probe 84 and the sample stirring rod 86 so as to be so close to one another at their respective lower positions 90 and 98, the sample probe 84 and sample stirring rod 86 can effectively be used within reaction cuvettes 54 which are much smaller than those used in prior art analyzing machines. The ability to use such small reaction cuvettes 54 results in significant reagent savings to the operator. It also allows the operator to conduct clinical analyses with very small samples.

The device of the invention further comprises a reagent probe arm assembly 108 such as shown in FIGS. 7A–7D. The reagent probe arm assembly 108 includes a reagent probe arm 110, a hollow reagent probe 112 and a rotatable reagent stirring rod 114. The reagent probe 112 has an internal chamber 116, an opened lower end 118 and an open upper end 120. A reagent probe pressure altering assembly 122 is provided to alternatively place pressure or a vacuum on the internal chamber 116. Preferably, the pressure altering assembly comprises a syringe 124.

The reagent probe 112 is disposed generally vertically in the reagent probe arm 110 and is movable by a reagent probe motor 126 between a lower reagent probe position and an upper reagent probe position.

The reagent stirring rod 114 has a lower end 128, an upper end 130 and a stirring rod paddle 132. The reagent stirring rod 114 is also disposed generally vertically in the reagent probe arm 110 and is movable by a reagent stirring rod motor 132 be between a lower reagent stirring rod position and an upper reagent stirring rod position. As is the case with respect to the sample probe 84 and the sample stirring rod 86, it is preferable that the raising and lowering of the reagent stirring rod 114 be independent of the raising and lowering of the reagent probe 112.

It is also preferable that the reagent stirring rod 114 and the reagent probe 112 be raised and lowered using a rack and pinion assembly 134. Such rack and pinion assembly 134 allows the reagent probe 112 and the reagent stirring rod 114 to be mounted close enough to one another to achieve the close proximities at their lower ends 118 and 128 described immediately below.

Like the sample probe 84 and the sample stirring rod 86, the reagent probe 112 and reagent stirring rod 114 are disposed within the reagent probe arm 110 at a slight angle with respect to one another. Preferably, this angle $\beta$ is between about 2.4° and about 2.6°. The reagent probe 112 and the reagent stirring rod 114 are angled towards one another for the same reason that the sample probe 84 and the sample stirring rod 86 are angled towards one another: that is to provide for a convergence of the lower ends 118 and 128 of the reagent probe 112 and the reagent stirring rod 114 to a distance between about 1.7 mm and about 5.3 mm, more preferably between about 1.7 and about 3.5 mm, most preferably between about 1.7 and about 3 mm. This close proximity of the lower ends 118 and 128 of the reagent probe 112 and the reagent stirring rod 114 allow the use of very small reaction cuvettes 54.

Preferably, both the sample probe arm 82 and the reagent probe arm 108 comprise level controllers (not shown) for determining the elevation of the probes 84 and 112 and/or the stirring rods 86 and 114 relative to a liquid level.

The machine of the invention 10 further comprises a cuvette wash station 130 attached to the body. The cuvette wash station 130 includes at least one hollow cuvette wash station probe 132 having an internal chamber 134, an open lower end 137 and an open upper end 139. The cuvette wash station 130 is disposed such that the cuvette wash station probe 132 is immediately above the cuvette washing site 60.

The cuvette wash station probe 132 is movable by a cuvette wash station motor (not shown) between a lower cuvette wash station probe position and an upper cuvette wash station probe position.

In the embodiment shown in FIG. 8, the cuvette wash station probe 132 comprises two concentrically disposed cuvette wash station probes 132a and 132b. One probe 132 is used to evacuate the contents of a cuvette and transmit such contents to a suitable disposal site 135. The other probe 132 is used to provide the cuvette with a washing solution.

The device of the invention further comprises a cuvette wash station probe supply and disposal assembly 136 for alternatively (1) providing pressurized washing liquid from a source of washing liquid to the cuvette washing station probe 132 for washing a cuvette 54 disposed at the cuvette washing site 60 and (2) providing a negative pressure to the interior chamber 134 of the cuvette wash station probe 132 for removing waste liquids from a cuvette 54 disposed within analyzing site 60 and for transferring such waste liquids to a suitable disposal site 135.

A preferred wash station probe supply and disposal assembly 136 comprises a waste trap assembly 138 shown in FIGS. 9A–9D. The waste trap assembly 138 comprises a waste trap reservoir 140 and a waste collector bowl 142 disposed below the waste trap reservoir 140. A vertically disposed connector conduit 144 connects the waste trap reservoir 140 in fluid communication with the waste collector bowl 142. The connector conduit 144 has an uppermost lip 146 over which waste liquids which collect within the waste trap reservoir 140 spill over into the waste collector bowl 142. The connector conduit 144 has a connector conduit check valve 148 for preventing the upward flow of liquids and pressurized air within the connector conduit 144 from the waste collector bowl 142 to the waste trap reservoir 140.

The waste trap reservoir 140 has an inlet port 150 in the upper portion of the waste trap reservoir 140 for receiving waste liquid from the cuvette wash station 130. The waste collector bowl 142 has an outlet port 152 in the bottom of the waste collector bowl 142 for draining liquid within the waste collector bowl 142 to a suitable waste disposal facility via a drain conduit 154. The drain conduit 154 has a drain conduit check valve 156 to prevent liquids from flowing back into the waste collector bowl 142 via the drain conduit 154.

A level sensor 158 is disposed within the waste collector bowl 142 for sensing the level of liquids within the waste collector bowl 142 and emitting a corresponding level sensor signal. In operation, the waste trap reservoir 140 is operatively connected to a source of vacuum. Also, the waste collector bowl 142 is operatively connected via a switch 160 to a source of vacuum and to a source of pressurized air.

The waste trap assembly 138 further comprises a waste trap controller (not shown) for receiving the level sensor 158 signal from the level sensor and using that signal to control the application of a vacuum and pressure to the waste collector bowl in the following way: (i) when the level of liquid within the waste collector bowl 142 is below a preselected set point, vacuum is applied to the waste collector bowl 142 to draw waste liquid from the waste trap reservoir 140 and (ii) when the level of liquid within the waste collector bowl 142 is at the preselected set point, pressure is applied to the waste collector bowl 142 to blow down waste liquid within the waste collector bowl 142 to the drain conduit 154.

The waste trap assembly connector conduit check valve 148 preferably comprises an inlet conduit 162, a valve seat 164 disposed within the inlet conduit 162 and in fluid tight communication therewith, an outlet conduit 166 disposed below the valve seat 164 and in fluid tight communication therewith and a plug 168 loosely disposed within the valve seat 164 such that (1) when the pressure within the inlet conduit is equal to or greater than the pressure within the outlet conduit 166, the plug 168 is not held tightly against the valve seat 164 so as to allow liquid waste within the inlet conduit 162 to gravitate into the outlet conduit 166 and (2) when the pressure within the inlet conduit 162 is less than the pressure within the outlet conduit 166, the plug 168 is held tightly against the valve seat 164 so as to prevent liquid waste within the inlet conduit 162 from gravitating into the outlet conduit 166 and to prevent pressurized air in the outlet conduit 166 from flowing through the inlet conduit 164 into the waste trap reservoir 140.

Preferably, the plug 168 is a flexible disk as shown in the drawings. The flexible disk has at least one central aperture 170 which is off-set from the inlet conduit 162.

Preferably, the waste trap 138 assembly further comprises (a) a vacuum source inlet port 172 disposed in the waste trap reservoir 140, the vacuum source inlet port 172 being connectable to a source of vacuum, (b) a three way valve 174 having a common port 176, a normally open port 178 and a normally closed port 180, (c) a first pressure source conduit 181 connected in fluid tight communication between the common port 176 and the waste collection bowl 142, (d) a second pressure source conduit 182 connected in fluid tight communication between the normally open port 178 and the waste trap reservoir 140, and (e) a third pressure source conduit 184 connected in fluid tight communication between the normally closed port 180 and a source of air pressure.

This waste trap assembly 138 provides significant advantages over prior art waste trap assemblies. The waste trap assembly 138 of the invention requires only one vacuum storage reservoir 140 and one vacuum pump. Moreover, a wash cycle need not be interrupted for liquid waste evacuations. Also, no external waste pump is required as is generally required by prior art systems. This is because the waste trap assembly 138 of the invention relies on air pressure to drive the waste out of the assembly. Some prior art systems also use pressurized air to force waste out of a waste trap assembly. However, such systems are wasteful of vacuum since each time the reservoir level signals for the three-way valve to switch, the entire vacuum contents of the reservoir are replaced by pressurized air to force waste to the pump. This can significantly slow down operation of the machine since replenishing the vacuum can take 16 seconds and more. Moreover, a relatively large vacuum pump is required.

Preferably, the analyzing machine 10 of the invention further comprises a controller 186 for controlling the operation of the motors, analyzers and bar code readers. Preferably, the controller 186 includes a digital computer which is also programmed to receive the results from the analyzer 68 and report those results to the operator in an efficient format.

In operation, the operator of a preferred embodiment of the analysis machine loads the reagent station 16 with premixed reagent from a kit. The kit includes one or more reagent containers 48 containing premixed reagent and a bar code card having bar-coded information thereon regarding the reagent within the kit.

After loading the reagent containers 48 into the reagent station 16, the operator places the bar-coded card 37 from the reagent kit on the forward wall 41 of the sample container rack 30 using the sample container rack retainer assembly 40. The operator instructs the sample station bar code reader 47 to read into the controller the bar-coded information contained on the bar-coded card 37. The operator then removes the bar-coded card 37 from the sample container 30.

The operator then loads the sample carousel 24 with sample containers 20 containing samples to be analyzed. The sample containers 20 are loaded into sample container racks 30 and the sample container racks 30 are attached to the exterior perimeter of the sample carousel 24. A label containing bar-coded information regarding the identity of each of the samples and the analyses to be run on each of the samples is attached to each sample container 20. The operator then places diluent containers 26 in the sample carousel 24 and places clean dilution sections 28 in the sample carousel 24. The operator then engages the machine 10 which carries out the following steps automatically.

The sample carousel 24 is rotated, making frequent stops. Whenever a container 20 is disposed in front of the sample station bar code reader 47, the bar code reader 47 reads the bar-coded information on the label on the sample container 20 and passes that information along to the controller 186.

The sample probe arm 82 moves the sample station probe 84 to a position immediately above the sample extraction site 22. The sample probe 84 is lowered from its upper probe position until the sample probe level controller senses the fact that the sample probe 84 is below the surface of the sample within the sample container 20 positioned at the sample extraction site 22.

The sample probe pressure altering assembly 92 is then caused to draw a vacuum in the sample probe internal chamber 88. This, in turn, causes sample within the sample container 20 to be drawn into the sample probe internal chamber 88. The sample probe 84 is then raised to its upper position and the sample probe arm 82 rotates to a position over one of the dilution cups 42. The sample probe 84 is again lowered into the dilution cup 42 and the sample probe pressure altering assembly 92 causes the sample within the sample probe 84 to be discharged into the dilution cup 42.

The sample probe arm 82 then rotates the sample probe 84 to a position immediately above one of the diluent containers 26 in the sample station 14. The sample probe 84 is lowered from its upper position to a position below the surface of the diluent in the diluent container 26 as sensed by the sample probe level controller. The pressure altering assembly 92 causes a vacuum to be drawn within the sample probe internal chamber 88 and diluent is drawn into the sample probe 84. The sample probe 84 is then raised to its upper position and the sample arm rotates the sample probe 84 to a position immediately above one of the dilution cups 42. The sample probe 84 is lowered into the dilution cup 42 and the pressure altering assembly 92 pressures the diluent out of the sample probe 84 and into the dilution cup 42.

The sample stirring rod 86 is then lowered into the dilution cup 42 and the sample stirring rod rotating motor 105 is engaged to mix the sample and the diluent.

Next, the sample probe 84 is again lowered into the dilution cup 42 and the diluent-sample mixture is drawn into the sample probe 84. The sample probe arm 82 then rotates the sample probe 84 to a position immediately above the cuvette 54 at the cuvette mixing site 56, the sample probe 84 is lowered into the cuvette 54, and the diluent-sample mixture is expelled from the sample probe 84 into the cuvette 54 by the sample probe pressure altering means 92.

Immediately before or after these steps, the controller 186 causes the reagent probe arm 110 to maneuver immediately above the appropriate reagent container 48 within the reagent extraction site 22 and the reagent probe 112 is lowered into the reagent container 48 and a quantity of reagent is drawn into the reagent probe 112. The reagent probe 112 is then raised to its upper position and the reagent arm 110 rotates the reagent probe 112 over the cuvette 54 at the cuvette mixing site 56. The reagent probe 112 is then lowered into the cuvette 54 and the reagent is discharged into the cuvette 54.

At this point, either the sample stirring rod 86 (or the reagent stirring rod 114 depending upon which stirring rod is immediately above the cuvette mixing site at this point in time) is lowered into the cuvette 54 and the rotating motor is engaged to agitate the reagent-sample mixture with the stirring rod paddle 102.After mixing, the stirring rod 86 is retracted to its upper position.

The controller 186 then causes the random access analyzing station carousel 62 to rotate the cuvette 54 having the reagent-sample mixture past the random access analyzing station analyzing site 58. At this analyzing site 58, the random access analyzing station analyzer 68 analyzes the contents of the cuvette 54 and transmits that information to the controller 186. Preferably, the controller 186 causes the cuvette 54 to pass through the random access analyzing station analyzing site 58 on numerous occasions and instructs the analyzer 68 to analyze the contents on each of those numerous occasions. By making numerous analyses of the same reagent-sample mixture, the results ultimately reportable by the controller 186 are therefore very precise in nature.

After the contents of the cuvette 54 are analyzed, the random access analyzer carousel 62 is rotated so that the cuvette 54 is immediately below the cuvette washing site 60. At the cuvette washing site 60, the cuvette wash station probe 132 is lowered into the cuvette 54 and the contents of the cuvette 54 are extracted out of the cuvette 54 and sent to suitable disposal using the cuvette wash probe supply and disposal assembly 136. The cuvette 54 is then washed with pressurized washing liquid and that liquid is also sent to disposal using the cuvette wash probe supply and disposal assembly 136. The cuvette 54 is then clean and ready for another analysis operation.

The controller 186 is preferably programmed to keep track of a large number of reaction cuvettes 54 in various stages of the analysis process. The controller 186 causes the random access analyzing station carousel 62 to rotate with great rapidity, moving any of the large number of active cuvettes 54 to the various cuvette sites for one or more of the various operations described above. In this way, the analyzing machine 10 can carry out a large number of analyses in a very small amount of time.

Periodically during normal operation of the machine, the controller 186 causes the random access analyzing station analyzer 68 to analyze the contents of the onboard control sample 78. If the results of this analysis suggests that the analyzer 68 is out of calibration, the analyzer 68 is automatically recalibrated.

The invention provides a uniquely accurate and reliable nephelometer and nephelometer/turbidimeter combination, without unduly increasing manufacturing costs or operating expenses.

Although the present invention has been described in considerable detail with reference to certain preferred versions thereof, other versions are possible. Therefore, the spirit and scope of the appended claims should not be limited to the description of the preferred versions contained herein.

What is claimed is:

1. A rate nephelometer and rate turbidimeter combination comprising:

(a) a laser for generating a laser beam having a first wave length;

(b) a first beam splitter positioned to direct the laser beam into a transparent reaction container along a specific light path;

(c) a laser control light detector positioned to detect light energy scattered from the laser beam by particles suspended in a liquid medium within the reaction container;

(d) a light emitting diode for generating a light beam having a second wave length and directing that light beam through the reaction container along the specific light path;

(e) a nephelometer light detector positioned along the specific light path on the opposite side of the reaction container from light emitting diode;

(f) a lens positioned between the reaction container and the nephelometer light detector for focusing the light beam to the nephelometer light detector; and (g) a second beam splitter positioned between reaction container and the lens for reflecting the laser bean away from the lens.

2. The combination of claim 1 wherein the laser is a visible diode laser emitting light at a wavelength between about 600 nm and about 850 nm.

3. The combination of claim 1 wherein the light emitting diode is capable of emitting light at a wavelength between about 850 nm and 1050 nm.

4. The combination of claim 1 wherein the laser is a visible diode laser capable of emitting between 5 milliwatts to 10 milliwatts of total light energy.

5. The rate nephelometer of claim 1 wherein the reaction container is a reaction cuvette.

6. A rate nephelometer and rate turbidimeter combination comprising:

(a) a laser for generating a polarized laser beam of variable energy intensity having a first wave length, the laser beam having a total light energy output, a first polarized moiety having a light energy and a second polarized moiety having a light energy;

(b) a laser control light detector for detecting light energy and generating a control signal corresponding to the quantity of said detected light energy;

(c) a first beam splitter positioned to direct a first portion of the first polarized moiety of the laser beam into a transparent reaction container along a specific light path and to direct a second portion of the first polarized moiety of the laser beam to the laser control light detector, the first beam splitter being constructed so that the light energy of the second portion of the first polarized moiety of the laser beam is a known fraction of the light energy of the first polarized moiety of the laser beam;

(d) a nephelometer light detector positioned to detect light energy scattered from the first portion of the first polarized moiety of the laser beam by particles suspended in a liquid medium within the reaction container;

(e) a polarizing filter for filtering out the second portion of the second polarized moiety of the laser beam without substantially affecting the first polarized moiety, the polarizing filter being positioned between the first beam splitter and the laser control light detector;

(f) a control circuit for controlling the total light energy output of the laser using the control signal generated by the laser control light detector;

(g) a light emitting diode for generating a light beam having a second wave length and directing that light beam through the reaction container along the specific light path;

(h) a turbidimeter light detector positioned along the specific light path on the opposite side of the reaction container from the light emitting diode;

(i) a lens positioned between the reaction container and the turbidimeter light detector for focusing the light beam to the turbidimeter light detector; and (j) a second beam splitter positioned between reaction container and the lens for reflecting the laser beam away from the lens.

7. The combination of claim 6 wherein the laser is a visible diode laser emitting light at a wavelength between about 600 nm and about 850 nm.

8. The combination of claim 6 wherein the light emitting diode emitting light at a wavelength between about 850 nm and about 1050 nm.

9. The rate nephelometer of claim 6 wherein the proportion of the first portion of the laser beam is between 50% to 99% of the total light energy output of the laser beam.

10. The rate nephelometer of claim 6 wherein the proportion of the first portion of the laser beam is between 95% to 97% percent of the total light energy output of the laser beam.

11. The rate nephelometer of claim 6 wherein the reaction container is a reaction cuvette.

12. The combination of claim 6 wherein the first polarized moiety of the polarized laser beam is an S-wave and the second polarized moiety of the polarized laser beam is the P-wave.

13. The combination of claim 6 wherein the first polarized moiety of the polarized laser beam is P-wave and the second polarized moiety of the polarized laser beam is S-wave.

14. The rate nephelometer of claim 6 wherein the proportion of the first polarized moiety in the first portion of the laser beam is between 90% to 99% of the total light energy output of the laser beam.

15. A device for determining at least one parameter of a liquid sample, the device comprising:

(a) a body;

(b) a sample station disposed within the body, the sample station being sized and dimensioned to retain a plurality of sample containers and having a sample extraction site, the sample station being movable within the body such that, when the sample station retains a plurality of sample containers, individual sample containers are capable of being moved to and away from the sample extraction site;

(c) a sample station motor for moving the sample station such that, when the sample station retains a plurality of sample containers, individual sample containers are alternatively moved to and away from the sample extraction site;

(d) a reagent station disposed within the body, the reagent station being sized and dimensioned to retain a plurality of reagent containers and having a reagent extraction site, the reagent station being movable within the body such that, when the reagent station retains a plurality of reagent containers, individual reagent containers are capable of being moved to and away from the reagent extraction site;

(e) a reagent station motor for moving the reagent station such that, when the reagent station retains a plurality of reagent containers, individual reagent containers are alternatively moved to and away from the reagent extraction site;

(f) a random access analyzing station disposed within the body, the random access analyzing station being sized and dimensioned to retain a plurality of cuvettes and having a cuvette mixing site and a cuvette washing site, the random access analyzing station being movable within the body such that, when the random access analyzing station retains a plurality of cuvettes, individual cuvettes are capable of being moved to and away from (1) the cuvette mixing site, (2) the cuvette washing site and (3) the random access analyzing station analyzing site;

(g) an analyzer disposed proximate to the random access analyzing station for analyzing a sample disposed within the cuvettes, the analyzer including a rate nephelometer and rate turbidimeter combination comprising:
  (i) a laser for generating a laser beam having a first wave length;
  (ii) a first beam splitter positioned to direct the laser beam into a transparent reaction cuvette along a specific light path;
  (iii) a laser control light detector positioned to detect light energy scattered from the laser beam by particles suspended in a liquid medium within the reaction cuvette;
  (iv) a light emitting diode for generating a light beam having a second wave length and directing that light beam through the reaction cuvette along the specific light path;
  (v) a nephelometer light detector positioned along the specific light path on the opposite side of the reaction cuvette from the light emitting diode;
  (vi) a lens positioned between the reaction cuvette and the nephelometer light detector for focusing the light beam to the nephelometer light detector; and
  (vii) a second beam splitter positioned between reaction cuvette and the lens for reflecting the laser beam away from the lens;

(h) a random access analyzing station motor for moving the random access analyzing station such that, when the random access analyzing station retains a plurality of cuvettes, individual cuvettes are alternatively moved to and away from (1) the cuvette mixing site, (2) the cuvette washing site and (3) the random access analyzing station analyzing site; and (i) sample transfer means for transferring a liquid sample from the sample extraction site and reagent from the reagent extraction site to a cuvette in the random access analyzing station.

16. The device of claim 15 wherein the laser is a visible diode laser emitting light at a wavelength between about 600 nm and about 850 nm.

17. The device of claim 15 wherein the light emitting diode emitting light at a wavelength between about 850 nm and about 1050 nm.

18. A device for determining at least one parameter of a liquid sample, the device comprising:
(a) a body;

(b) a sample station disposed within the body, the sample station being sized and dimensioned to retain a plurality of sample containers and having a sample extraction site, the sample station being movable within the body such that, when the sample station retains a plurality of sample containers, individual sample containers are capable of being moved to and away from the extraction site;

(c) a sample station motor for moving the sample station such that, when the sample station retains a plurality of sample containers, individual sample containers are alternatively moved to and away from the sample extraction site;

(d) a reagent station disposed within the body, the reagent station being sized and dimensioned to retain a plurality of reagent containers and having a reagent extraction site, the reagent station being movable within the body such that, when the reagent station retains a plurality of reagent containers, individual reagent containers are capable of being moved to and away from the reagent extraction site;

(e) a reagent station motor for moving the reagent station such that, when the reagent station retains a plurality of reagent containers, individual reagent containers are alternatively moved to and away from the reagent extraction site;

(f) a random access analyzing station disposed within the body, the random access analyzing station being sized and dimensioned to retain a plurality of cuvettes and having a cuvette mixing site and a cuvette washing site, the random access analyzing station being movable within the body such that, when the random access analyzing station retains a plurality of cuvettes, individual cuvettes are capable of being moved to and away from (1) the cuvette mixing site, (2) the cuvette washing site and (3) the random access analyzing station analyzing site;

(g) an analyzer disposed proximate to the random access analyzing station for analyzing a sample disposed within the cuvettes, the analyzer including a rate nephelometer and rate turbidimeter combination comprising:
  (i) a laser for generating a laser beam having a first wave length;
  (ii) a first beam splitter positioned to direct the laser beam into a transparent reaction cuvette along a specific light path;
  (iii) a laser control light detector positioned to detect light energy scattered from the laser beam by particles suspended in a liquid medium within the reaction cuvette;
  (iv) a light emitting diode for generating a light beam having a second wave length and directing that light beam through the reaction cuvette along the specific light path;
  (v) a nephelometer light detector positioned along the specific light path on the opposite side of the reaction cuvette from the light emitting diode;
  (vi) a lens positioned between the reaction cuvette and the nephelometer light detector for focusing the light beam to the nephelometer light detector; and
  (vii) a second beam splitter positioned between reaction cuvette and the lens for reflecting the laser beam away from the lens;

(h) a random access analyzing station motor for moving the random access analyzing station such that, when the random access analyzing station retains a plurality of cuvettes, individual cuvettes are alternatively moved to and away from (1) the cuvette mixing site, (2) the cuvette washing site and (3) the random access analyzing station analyzing site;

(i) a sample probe arm assembly attached to the body, the sample probe arm assembly including (1) a sample probe arm, (2) a hollow sample probe having an internal chamber, an open lower end and an open upper end and (3) an elongate rotatable sample stirring rod having a lower end and an upper end, the lower end of the sample stirring rod including a sample stirring rod paddle attached thereto, the sample probe and the sample stirring rod being disposed generally vertically in close proximity to one another, the sample probe being vertically movable between a lower sample probe position and an upper sample probe position, the sample stirring rod being movable independent of the sample probe between a lower sample stirring rod position and an upper sample stirring rod position, the sample probe arm being movable between a first sample probe arm position wherein the sample probe is immediately above the sample extraction site and a second sample probe arm position wherein the sample probe is immediately above the cuvette mixing site;

(j) a sample probe arm motor for moving the sample probe arm between the first sample probe arm position and the second sample probe arm position;

(k) a sample probe positioning motor for moving the sample probe between the lower sample probe position and the upper sample probe position;

(l) a sample stirring rod positioning motor for moving the sample stirring rod between the lower sample stirring rod position and the upper sample stirring rod position;

(m) a sample stirring rod rotating motor for rotating the sample stirring rod;

(n) sample probe pressure altering means for alternatively applying a positive pressure and a negative pressure to the interior chamber of the sample probe;

(o) a reagent probe arm assembly attached to the body, the reagent probe arm assembly including (1) a reagent probe arm, (2) a hollow reagent probe having an internal chamber, an open lower end and an open upper end and (3) an elongate rotatable reagent stirring rod having a lower end and an upper end, the lower end of the reagent stirring rod including a reagent stirring rod paddle attached thereto, the reagent probe and the reagent stirring rod being disposed generally vertically in close proximity to one another, the reagent probe being vertically movable between a lower reagent probe position and an upper reagent probe position, the reagent stirring rod being movable independent of the reagent probe between a lower reagent stirring rod position and an upper reagent stirring rod position, the reagent probe arm being movable between a first reagent probe arm position wherein the reagent probe is immediately above the reagent extraction site and a second reagent probe arm position wherein the reagent probe is immediately above the cuvette mixing site;

(p) a reagent probe arm motor for moving the reagent probe arm between the first reagent probe arm position and the second reagent probe arm position;

(q) a reagent probe positioning motor for moving the reagent probe between the lower reagent probe position and the upper reagent probe position;

(r) a reagent stirring rod positioning motor for moving the reagent stirring rod between the lower reagent stirring rod position and the upper reagent stirring rod position;

(s) a reagent stirring rod rotating motor for rotating the reagent stirring rod;

(t) reagent probe pressure altering means for alternatively applying a positive pressure and a negative pressure to the interior chamber of the reagent probe;

(u) a cuvette wash station attached to the body, the cuvette wash station including a hollow cuvette wash station probe having an internal chamber, an open lower end and an open upper end, the cuvette wash station being disposed such that the cuvette wash station probe is immediately above the cuvette washing site;

(v) a cuvette wash station probe positioning motor for moving the cuvette wash station probe between the lower cuvette wash station probe position and the upper cuvette wash station probe position; and (w) cuvette wash station probe supply and disposal assembly for alternatively (1) providing pressurized washing liquid from a source of washing liquid to the cuvette wash station probe for washing a cuvette disposed within the random access analyzing station at the cuvette washing site and (2) providing a negative pressure to the interior chamber of the cuvette wash station probe for removing waste liquids from a cuvette disposed within the random access analyzing station at the analyzing site and for transferring such waste liquids to a disposal site.

19. The device of claim 18 wherein the laser is a visible diode laser emitting light at a wavelength between about 600 nm and about 850 nm.

20. The device of claim 18 wherein the light emitting diode emitting light at a wavelength between about 850 nm and about 1050 nm.

21. A device for determining at least one parameter of a liquid sample, the device comprising:

(a) a body;

(b) a sample station disposed within the body, the sample station being sized and dimensioned to retain a plurality of sample containers and having a sample extraction site, the sample station being movable within the body such that, when the sample station retains a plurality of sample containers, individual sample containers are capable of being moved to and away from the sample extraction site;

(c) a sample station motor for moving the sample station such that, when the sample station retains a plurality of sample containers, individual sample containers are alternatively moved to and away from the sample extraction site;

(d) a reagent station disposed within the body, the reagent station being sized and dimensioned to retain a plurality of reagent containers and having a reagent extraction site, the reagent station being movable within the body such that, when the reagent station retains a plurality of reagent containers, individual reagent containers are capable of being moved to and away from the reagent extraction site;

(e) a reagent station motor for moving the reagent station such that, when the reagent station retains a plurality of reagent containers, individual reagent containers are alternatively moved to and away from the reagent extraction site;

(f) a random access analyzing station disposed within the body, the random access analyzing station being sized and dimensioned to retain a plurality of cuvettes and having a cuvette mixing site and a cuvette washing site, the random access analyzing station being movable within the body such that, when the random access analyzing station retains a plurality of cuvettes, individual cuvettes are capable of being moved to and away from (1) the cuvette mixing site, (2) the cuvette washing site and (3) the random access analyzing station analyzing site;

(g) an analyzer disposed proximate to the random access analyzing station for analyzing a sample disposed within the cuvettes, the analyzer including a rate nephelometer and rate turbidimeter combination comprising:

(i) a laser for generating a polarized laser beam of variable energy intensity having a first wave length, the laser beam having a total light energy output, a first polarized moiety having a light energy and a second polarized moiety having a light energy;

(ii) a laser control light detector for detecting light energy and generating a control signal corresponding to the quantity of said detected light energy;

(iii) a first beam splitter positioned to direct a first portion of the first polarized moiety of the laser beam into a transparent reaction cuvette along a specific light path and to direct a second portion of the first polarized moiety of the laser beam to the laser control light detector, the first beam splitter being constructed so that the light energy of the second portion of the first polarized moiety of the laser beam is a known fraction of the total light energy output of the laser beam;

(iv) a nephelometer light detector positioned to detect light energy scattered from the first portion of the first polarized moiety of the laser beam by particles suspended in a liquid medium within the reaction cuvette;

(v) a polarizer for filtering out the second portion of the second polarized moiety of the laser beam without substantially affecting the first polarized moiety, the polarizer being positioned between the first beam splitter and the laser control light detector;

(vi) a control circuit for controlling the total light energy output of the laser using the control signal generated by the laser control light detector;

(vii) a light emitting diode for generating a light beam having a second wave length and directing that light beam through the reaction cuvette along the specific light path;

(viii) a turbidimeter light detector positioned along the specific light path on the opposite side of the reaction cuvette from the light emitting diode;

(ix) a lens positioned between the reaction cuvette and the turbidimeter light detector for focusing the light beam to the turbidimeter light detector; and (x) a second beam splitter positioned between reaction cuvette and the lens for reflecting the laser beam away from the lens;

(h) a random access analyzing station motor for moving the random access analyzing station such that, when the random access analyzing station retains a plurality of cuvettes, individual cuvettes are alternatively moved to and away from (1) the cuvette mixing site, (2) the cuvette washing site and (3) the random access analyzing station analyzing site; and (i) sample transfer means for transferring a liquid sample from the sample extraction site and reagent from the reagent extraction site to a cuvette in the random access analyzing station.

22. The device of claim 21 wherein the laser is a visible diode laser emitting light at a wavelength between about 600 nm and about 850 nm.

23. The device of claim 21 wherein the light emitting diode emitting light at a wavelength between about 850 nm and about 1050 nm.

24. The device of claim 21 wherein the first polarized moiety of the polarized laser beam is the S-wave moiety of the polarized laser beam and the second polarized moiety of the polarized laser beam is the P-wave moiety of the polarized laser beam.

25. The device of claim 21 wherein the proportion of the first portion of the laser beam is between 90% to 99% of the total light energy output of the laser beam.

26. A device for determining at least one parameter of a liquid sample, the device comprising:

(a) a body;

(b) a sample station disposed within the body, the sample station being sized and dimensioned to retain a plurality of sample containers and having a sample extraction site, the sample station being movable within the body such that, when the sample station retains a plurality of sample containers, individual sample containers are capable of being moved to and away from the sample extraction site;

(c) a sample station motor for moving the sample station such that, when the sample station retains a plurality of sample containers, individual sample containers are alternatively moved to and away from the sample extraction site;

(d) a reagent station disposed within the body, the reagent station being sized and dimensioned to retain a plurality of reagent containers and having a reagent extraction site, the reagent station being movable within the body such that, when the reagent station retains a plurality of reagent containers, individual reagent containers are capable of being moved to and away from the reagent extraction site;

(e) a reagent station motor for moving the reagent station such that, when the reagent station retains a plurality of reagent containers, individual reagent containers are alternatively moved to and away from the reagent extraction site;

(f) a random access analyzing station disposed within the body, the random access analyzing station being sized and dimensioned to retain a plurality of cuvettes and having a cuvette mixing site and a cuvette washing site, the random access analyzing station being movable within the body such that, when the random access analyzing station retains a plurality of cuvettes, individual cuvettes are capable of being moved to and away from (1) the cuvette mixing site, (2) the cuvette washing site and (3) the random access analyzing station analyzing site;

(g) an analyzer disposed proximate to the random access analyzing station for analyzing a sample disposed within the cuvettes, the analyzer including a rate nephelometer and rate turbidimeter combination comprising:

(i) a laser for generating a polarized laser beam of variable energy intensity having a first wave length, the laser beam having a total light energy, a first polarized moiety having a light energy and a second polarized moiety having a light energy;

(ii) a laser control light detector for detecting light energy and generating a control signal corresponding to the quantity of said detected light energy;

(iii) a first beam splitter positioned to direct a first portion of the first polarized moiety of the laser beam into a transparent reaction cuvette along a specific light path and to direct a second portion of the first polarized moiety of the laser beam to the laser control light detector, the first beam splitter being constructed so that the light energy of the second portion of the first polarized moiety of the laser beam is a known fraction of the total light energy output of the laser beam;

(iv) a nephelometer light detector positioned to detect light energy scattered from the first portion of the first polarized moiety of the laser beam by particles suspended in a liquid medium within the reaction cuvette;

(v) a polarizer for filtering out the second portion of the second polarized moiety of the laser beam without substantially affecting the first polarized moiety, the polarizer being positioned between the first beam splitter and the laser control light detector;

(vi) a control circuit for controlling the total light energy output of the laser using the control signal generated by the laser control light detector;

(vii) a light emitting diode for generating a light beam having a second wave length and directing that light beam through the reaction cuvette along the specific light path;

(viii) a turbidimeter light detector positioned along the specific light path on the opposite side of the reaction cuvette from the light emitting diode;

(ix) a lens positioned between the reaction cuvette and the turbidimeter light detector for focusing the light beam to the turbidimeter light detector; and (x) a second beam splitter positioned between reaction cuvette and the lens for reflecting the laser beam away from the lens;

(h) a random access analyzing station motor for moving the random access analyzing station such that, when the random access analyzing station retains a plurality of cuvettes, individual cuvettes are alternatively moved to and away from (1) the cuvette mixing site, (2) the cuvette washing site and (3) the random access analyzing station analyzing site;

(i) a sample probe arm assembly attached to the body, the sample probe arm assembly including (1) a sample probe arm, (2) a hollow sample probe having an internal chamber, an open lower end and an open upper end and (3) an elongate rotatable sample stirring rod having a lower end and an upper end, the lower end of the sample stirring rod including a sample stirring rod paddle attached thereto, the sample probe and the sample stirring rod being disposed generally vertically in close proximity to one another, the sample probe being vertically movable between a lower sample probe position and an upper sample probe position, the sample stirring rod being movable independent of the sample probe between a lower sample stirring rod position and an upper sample stirring rod position, the sample probe arm being movable between a first sample probe arm position wherein the sample probe is immediately above the sample extraction site and a second sample probe arm position wherein the sample probe is immediately above the cuvette mixing site;

(j) a sample probe arm motor for moving the sample probe arm between the first sample probe arm position and the second sample probe arm position;

(k) a sample probe positioning motor for moving the sample probe between the lower sample probe position and the upper sample probe position;

(l) a sample stirring rod positioning motor for moving the sample stirring rod between the lower sample stirring rod position and the upper sample stirring rod position;

(m) a sample stirring rod rotating motor for rotating the sample stirring rod;

(n) sample probe pressure altering means for alternatively applying a positive pressure and a negative pressure to the interior chamber of the sample probe;

(o) a reagent probe arm assembly attached to the body, the reagent probe arm assembly including (1) a reagent probe arm, (2) a hollow reagent probe having an internal chamber, an open lower end and an open upper end and (3) an elongate rotatable reagent stirring rod having a lower end and an upper end, the lower end of the reagent stirring rod including a reagent stirring rod paddle attached thereto, the reagent probe and the reagent stirring rod being disposed generally vertically in close proximity to one another, the reagent probe being vertically movable between a lower reagent probe position and an upper reagent probe position, the reagent stirring rod being movable independent of the reagent probe between a lower reagent stirring rod position and an upper reagent stirring rod position, the reagent probe arm being movable between a first reagent probe arm position wherein the reagent probe is immediately above the reagent extraction site and a second reagent probe arm position wherein the reagent probe is immediately above the cuvette mixing site;

(p) a reagent probe arm motor for moving the reagent probe arm between the first reagent probe arm position and the second reagent probe arm position;

(q) a reagent probe positioning motor for moving the reagent probe between the lower reagent probe position and the upper reagent probe position;

(r) a reagent stirring rod positioning motor for moving the reagent stirring rod between the lower reagent stirring rod position and the upper reagent stirring rod position;

(s) a reagent stirring rod rotating motor for rotating the reagent stirring rod;

(t) reagent probe pressure altering means for alternatively applying a positive pressure and a negative pressure to the interior chamber of the reagent probe;

(u) a cuvette wash station attached to the body, the cuvette wash station including a hollow cuvette wash station probe having an internal chamber, an open lower end and an open upper end, the cuvette wash station being disposed such that the cuvette wash station probe is immediately above the cuvette washing site;

(v) a cuvette wash station probe positioning motor for moving the cuvette wash station probe between the lower cuvette wash station probe position and the upper cuvette wash station probe position; and (w) cuvette wash station probe supply and disposal assembly for alternatively (1) providing pressurized washing liquid from a source of washing liquid to the cuvette wash station probe for washing a cuvette disposed within the random access analyzing station at the cuvette washing site and (2) providing a negative pressure to the interior chamber of the cuvette wash station probe for removing waste liquids from a cuvette disposed within the random access analyzing station at the analyzing site and for transferring such waste liquids to a disposal site.

27. The device of claim 26 wherein the laser is a visible diode laser emitting light at a wavelength between about 600 nm and about 850 nm.

28. The device of claim 26 wherein the light emitting diode emitting light at a wavelength between about 850 nm and about 1050 nm.

29. The device of claim 26 wherein the first polarized moiety of the polarized laser beam is the S-wave moiety of the polarized laser beam and the second polarized moiety of the polarized laser beam is the P-wave moiety of the polarized laser beam.

30. The device of claim 26 wherein the proportion of the first portion of the laser beam is between 90% to 99% of the total light energy output of the laser beam.

* * * * *